(12) United States Patent
Lim et al.

(10) Patent No.: US 12,207,946 B2
(45) Date of Patent: Jan. 28, 2025

(54) SURGICAL PLATFORM SYSTEM

(71) Applicant: Warsaw Orthopedic, Inc., Warsaw, IN (US)

(72) Inventors: Roy K. Lim, Memphis, TN (US); Mark C. Dace, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 363 days.

(21) Appl. No.: 17/740,588

(22) Filed: May 10, 2022

(65) Prior Publication Data
US 2023/0363715 A1    Nov. 16, 2023

(51) Int. Cl.
*A61G 13/04*     (2006.01)
*A61B 5/00*      (2006.01)
*A61B 34/30*     (2016.01)

(52) U.S. Cl.
CPC .............. *A61B 5/702* (2013.01); *A61B 5/704* (2013.01); *A61B 34/30* (2016.02)

(58) Field of Classification Search
CPC .... A61B 5/702; A61B 5/704; A61G 13/0054; A61G 13/04; A61G 13/06; A61G 13/08; A61G 7/008; A61G 2200/325
See application file for complete search history.

(56) References Cited

U.S. PATENT DOCUMENTS

| | | |
|---|---|---|
| 2,691,979 A | 10/1954 | Watson |
| 3,060,925 A | 10/1962 | Honsaker et al. |
| 3,227,440 A | 1/1966 | Scott |
| 3,293,667 A | 12/1966 | Ohrberg |
| 3,306,287 A | 2/1967 | Arp |
| 3,389,702 A | 6/1968 | Kennedy |
| 3,828,377 A | 8/1974 | Fary, Sr. |

(Continued)

FOREIGN PATENT DOCUMENTS

| | | |
|---|---|---|
| EP | 3158986 | 4/2017 |
| EP | 3434248 | 1/2019 |

(Continued)

OTHER PUBLICATIONS

International Search Report and Written Opinion dated Jul. 19, 2023 in PCT/IB2023/054288.

(Continued)

*Primary Examiner* — Fredrick C Conley

(57) ABSTRACT

A surgical platform system including a first platform portion, a second platform portion, and a support portion is provided. The support platform supports the first platform portion, and can be moveable relative to a surgical robotic system supporting the second platform portion. With the support portion and the first platform portion positioned relative to the surgical robotic system, the first platform portion supporting a first portion of the patient and the second platform portion supporting a second portion of the patient can be adjusted relative to one another to correspondingly adjust positions/orientations of the first portion and the second portion of the patient. To illustrate, using an end portion supporting the first platform portion, the first platform portion can be rotated about a vertical axis and moved side to side to adjust the position/orientation thereof relative to the second platform portion.

20 Claims, 23 Drawing Sheets

(56) References Cited

U.S. PATENT DOCUMENTS

| | | |
|---|---|---|
| 4,029,089 A | 6/1977 | Mulhlland |
| 4,194,257 A | 3/1980 | Martin et al. |
| 4,627,119 A | 12/1986 | Hachey et al. |
| 4,655,200 A | 4/1987 | Knight |
| 4,705,026 A | 11/1987 | Chaussy |
| 4,866,796 A | 9/1989 | Robinson |
| 4,872,656 A | 10/1989 | Brendgord |
| 4,901,384 A | 2/1990 | Eary |
| 4,915,101 A | 4/1990 | Cuccia |
| 5,009,407 A | 4/1991 | Watanabe |
| 5,013,018 A | 5/1991 | Sicek |
| 5,088,706 A | 2/1992 | Jackson |
| 5,103,511 A | 4/1992 | Sequin |
| 5,131,106 A | 7/1992 | Jackson |
| 5,362,302 A | 11/1994 | Jenson et al. |
| 5,390,383 A | 2/1995 | Carn |
| 5,410,769 A | 5/1995 | Waterman |
| 5,444,882 A | 8/1995 | Andrews |
| 5,613,254 A | 3/1997 | Clayman |
| 5,642,302 A | 6/1997 | Dumont |
| 5,860,899 A | 1/1999 | Rassman |
| 5,991,651 A | 11/1999 | LaBarbera |
| 6,003,176 A | 12/1999 | Wasley |
| 6,076,525 A | 6/2000 | Hoffman |
| 6,112,349 A | 9/2000 | Connolly |
| 6,154,901 A | 12/2000 | Carr |
| 6,260,220 B1 | 7/2001 | Lamb |
| 6,295,671 B1 | 10/2001 | Reesby et al. |
| 6,311,349 B1 | 11/2001 | Kazakia |
| 6,367,104 B1 | 4/2002 | Fallbo, Sr. et al. |
| 6,378,149 B1 | 4/2002 | Sanders et al. |
| 6,516,483 B1 | 2/2003 | VanSteenburg |
| 6,566,833 B2 | 5/2003 | Barlett |
| 6,615,430 B2 | 9/2003 | Heimbrock |
| 6,671,905 B2 | 1/2004 | Bartlett et al. |
| 6,681,423 B2 | 1/2004 | Zachrisson |
| 6,701,553 B1 | 3/2004 | Hand et al. |
| 6,701,554 B2 | 3/2004 | Heimbrock |
| 6,701,558 B2 | 3/2004 | VanSteenburg |
| 6,715,169 B2 | 4/2004 | Niederkrom |
| 6,728,983 B2 | 5/2004 | Bartlett et al. |
| 6,732,390 B2 | 5/2004 | Krywiczanin |
| 6,739,006 B2 | 5/2004 | Borders et al. |
| 6,820,621 B2 | 11/2004 | DeMayo |
| 6,874,181 B1 | 4/2005 | Connolly et al. |
| 6,934,986 B2 | 8/2005 | Krywiczanin et al. |
| 6,941,951 B2 | 9/2005 | Hubert et al. |
| 6,966,081 B1 | 11/2005 | Sharps |
| 7,100,225 B1 | 9/2006 | Bailey |
| 7,152,261 B2 | 12/2006 | Jackson |
| 7,189,214 B1 | 3/2007 | Saunders |
| 7,219,379 B2 | 5/2007 | Krywiczanin et al. |
| 7,234,180 B2 | 6/2007 | Horton et al. |
| 7,290,302 B2 | 11/2007 | Sharps |
| 7,343,635 B2 | 3/2008 | Jackson |
| 7,426,930 B1 | 9/2008 | Bailey |
| 7,472,440 B2 | 1/2009 | Bartlett et al. |
| 7,484,253 B1 | 2/2009 | Coppens |
| 7,496,980 B2 | 3/2009 | Sharps |
| 7,565,708 B2 | 7/2009 | Jackson |
| 7,600,281 B2 | 10/2009 | Skripps |
| 7,669,262 B2 | 3/2010 | Skripps |
| 7,739,762 B2 | 6/2010 | Lamb et al. |
| 7,882,583 B2 | 2/2011 | Skripps |
| 8,060,960 B2 | 11/2011 | Jackson |
| 8,118,029 B2 | 2/2012 | Gneiting et al. |
| 8,286,283 B2 | 10/2012 | Copeland et al. |
| 8,286,637 B2 | 10/2012 | Kaska |
| 8,381,335 B2 | 2/2013 | Ahlman |
| 8,413,660 B2 | 4/2013 | Weinstein et al. |
| 8,439,948 B1 | 5/2013 | King |
| 8,443,473 B2 | 5/2013 | Maxwell |
| 8,584,281 B2 | 11/2013 | Diel et al. |
| 8,635,725 B2 | 1/2014 | Tannoury et al. |
| 8,677,529 B2 | 3/2014 | Jackson |
| 8,707,484 B2 | 4/2014 | Jackson et al. |
| 8,978,180 B2 | 3/2015 | Jackson |
| 9,072,646 B2 | 7/2015 | Skripps et al. |
| 9,180,062 B2 | 11/2015 | Jackson |
| 9,186,291 B2 | 11/2015 | Jackson et al. |
| 9,226,865 B2 | 1/2016 | Jackson et al. |
| 9,265,680 B2 | 2/2016 | Sharps |
| 9,295,433 B2 | 3/2016 | Jackson et al. |
| 9,308,145 B2 | 4/2016 | Jackson |
| 9,339,430 B2 | 5/2016 | Jackson et al. |
| 9,358,170 B2 | 6/2016 | Jackson |
| 9,402,775 B2 | 8/2016 | Jackson et al. |
| 9,414,982 B2 | 8/2016 | Jackson |
| 9,468,576 B2 | 10/2016 | Jackson |
| 9,498,397 B2 | 11/2016 | Hight et al. |
| 9,522,078 B2 | 12/2016 | Pizzini |
| 9,554,959 B2 | 1/2017 | Carn |
| 9,622,928 B2 | 4/2017 | Jackson et al. |
| 9,642,760 B2 | 5/2017 | Jackson et al. |
| 9,655,793 B2 | 5/2017 | Hertz |
| 9,700,476 B2 | 7/2017 | Hoel et al. |
| 9,713,562 B2 | 7/2017 | Perlman et al. |
| 9,744,089 B2 | 8/2017 | Jackson |
| 9,849,054 B2 | 12/2017 | Jackson |
| 9,937,006 B2 | 4/2018 | Skripps et al. |
| 9,993,380 B2 | 6/2018 | Jackson |
| 10,136,863 B2 | 11/2018 | Kaiser et al. |
| 10,314,758 B2 | 6/2019 | Dolliver et al. |
| 10,342,722 B2 | 7/2019 | Garrido |
| 10,406,054 B1 | 9/2019 | Scholl et al. |
| 10,426,684 B2 | 10/2019 | Dubois et al. |
| 10,492,973 B2 * | 12/2019 | Drake .................. A61G 7/075 |
| 10,531,998 B2 | 1/2020 | Jackson et al. |
| 10,543,142 B2 | 1/2020 | Lim et al. |
| 10,548,796 B2 | 2/2020 | Lim et al. |
| 10,576,006 B2 | 3/2020 | Lim et al. |
| 10,695,252 B2 | 6/2020 | Jackson |
| 10,722,413 B2 | 7/2020 | Lim et al. |
| 10,729,607 B2 | 8/2020 | Jackson |
| 10,751,240 B2 | 8/2020 | Lim et al. |
| 10,835,438 B2 | 11/2020 | Jackson |
| 10,835,439 B2 | 11/2020 | Lim et al. |
| 10,849,809 B2 | 12/2020 | Lim et al. |
| 10,874,570 B2 | 12/2020 | Lim et al. |
| 10,881,570 B2 | 1/2021 | Lim et al. |
| 10,888,484 B2 | 1/2021 | Lim et al. |
| 10,893,996 B2 | 1/2021 | Lim et al. |
| 10,898,401 B2 | 1/2021 | Lim et al. |
| 10,900,448 B2 | 1/2021 | Lim et al. |
| 2002/0138905 A1 | 10/2002 | Barltett et al. |
| 2002/0138906 A1 | 10/2002 | Barltett et al. |
| 2002/0157186 A1 | 10/2002 | VanSteenburg |
| 2003/0140419 A1 | 7/2003 | Barltett et al. |
| 2003/0140420 A1 | 7/2003 | Niederkrom |
| 2003/0145382 A1 | 8/2003 | Krywiczanin |
| 2003/0178027 A1 | 9/2003 | DeMayo et al. |
| 2004/0010849 A1 | 1/2004 | Krywiczanin et al. |
| 2004/0133979 A1 | 7/2004 | Newkirk et al. |
| 2004/0133983 A1 | 7/2004 | Newkirk |
| 2005/0181917 A1 | 8/2005 | Dayal |
| 2006/0037141 A1 | 2/2006 | Krywiczanin et al. |
| 2006/0123546 A1 | 6/2006 | Horton |
| 2006/0162076 A1 | 7/2006 | Bartlett et al. |
| 2006/0162084 A1 | 7/2006 | Mezue |
| 2006/0185090 A1 | 8/2006 | Jackson |
| 2008/0034502 A1 | 2/2008 | Copeland et al. |
| 2008/0134434 A1 | 6/2008 | Celauro |
| 2008/0222811 A1 | 9/2008 | Gilbert et al. |
| 2009/0070936 A1 | 3/2009 | Henderson |
| 2009/0139030 A1 | 6/2009 | Yang |
| 2009/0248041 A1 | 10/2009 | Williams et al. |
| 2010/0037397 A1 | 2/2010 | Wood |
| 2010/0192300 A1 | 8/2010 | Tannoury |
| 2010/0293719 A1 | 11/2010 | Klemm et al. |
| 2011/0099716 A1 | 5/2011 | Jackson |
| 2011/0107516 A1 * | 5/2011 | Jackson .................. A61G 13/04 5/608 |
| 2012/0103344 A1 | 5/2012 | Hunter |
| 2012/0144589 A1 | 6/2012 | Skripps et al. |

(56) References Cited

U.S. PATENT DOCUMENTS

| | | |
|---|---|---|
| 2012/0255122 A1 | 10/2012 | Diel et al. |
| 2013/0111666 A1 | 5/2013 | Jackson |
| 2013/0191994 A1 | 8/2013 | Bellows et al. |
| 2013/0283526 A1 | 10/2013 | Gagliardi |
| 2013/0307298 A1 | 11/2013 | Meiki |
| 2014/0020183 A1 | 1/2014 | Dominick |
| 2014/0059773 A1 | 3/2014 | Carn |
| 2014/0068861 A1 | 3/2014 | Jackson |
| 2014/0109316 A1 | 4/2014 | Jackson et al. |
| 2014/0130258 A1 | 5/2014 | Kobuss |
| 2014/0137327 A1 | 5/2014 | Tannoury et al. |
| 2015/0038982 A1 | 2/2015 | Kilroy et al. |
| 2015/0044956 A1 | 2/2015 | Hacker |
| 2015/0245971 A1 | 9/2015 | Bernardoni et al. |
| 2015/0272681 A1 | 10/2015 | Skripps et al. |
| 2016/0000621 A1 | 1/2016 | Jackson |
| 2016/0081582 A1 | 3/2016 | Rapoport |
| 2016/0089287 A1 | 3/2016 | Buerstner |
| 2016/0193099 A1 | 7/2016 | Drake |
| 2016/0317373 A1 | 11/2016 | Jackson et al. |
| 2017/0027797 A1 | 2/2017 | Dolliver et al. |
| 2017/0049651 A1 | 2/2017 | Lim |
| 2017/0049653 A1 | 2/2017 | Lim |
| 2017/0079864 A1 | 3/2017 | Riley |
| 2017/0112698 A1 | 4/2017 | Hight et al. |
| 2017/0135891 A1 | 5/2017 | Kettner |
| 2017/0151115 A1 | 6/2017 | Jackson |
| 2017/0341232 A1 | 11/2017 | Perplies |
| 2017/0348171 A1 | 12/2017 | Jackson |
| 2018/0116891 A1 | 5/2018 | Beale et al. |
| 2018/0185106 A1 | 7/2018 | Itkowitz et al. |
| 2018/0185228 A1 | 7/2018 | Catacchio et al. |
| 2018/0193104 A1 | 7/2018 | Beale et al. |
| 2018/0207044 A1 | 7/2018 | Sabet et al. |
| 2018/0363596 A1 | 12/2018 | Lim et al. |
| 2019/0000702 A1 | 1/2019 | Lim et al. |
| 2019/0000707 A1 | 1/2019 | Lim et al. |
| 2019/0046381 A1 | 2/2019 | Lim et al. |
| 2019/0046383 A1 | 2/2019 | Lim et al. |
| 2019/0209409 A1 | 7/2019 | Jackson et al. |
| 2019/0374420 A1 | 12/2019 | Lehman et al. |
| 2020/0000668 A1 | 1/2020 | Lim et al. |
| 2020/0060913 A1 | 2/2020 | Lim et al. |
| 2020/0060914 A1 | 2/2020 | Lim et al. |
| 2020/0060915 A1 | 2/2020 | Lim et al. |
| 2020/0138660 A1 | 5/2020 | Jackson |
| 2020/0170868 A1 | 6/2020 | Jackson |
| 2020/0188208 A1 | 6/2020 | Lim et al. |
| 2020/0138659 A1 | 7/2020 | Lim et al. |
| 2020/0281788 A1 | 9/2020 | Lim et al. |
| 2020/0297568 A1 | 9/2020 | Lim et al. |
| 2020/0337923 A1 | 10/2020 | Lim et al. |
| 2020/0337926 A1 | 10/2020 | Lim et al. |
| 2020/0337927 A1* | 10/2020 | Lim ............ A61G 13/04 |
| 2020/0360214 A1 | 11/2020 | Lim et al. |
| 2022/0008016 A1 | 1/2022 | Harrison et al. |
| 2022/0409311 A1 | 12/2022 | Tadano et al. |

FOREIGN PATENT DOCUMENTS

| | | |
|---|---|---|
| EP | 3909539 | 11/2021 |
| JP | 2018069048 | 5/2018 |
| JP | 6449958 | 12/2018 |
| WO | WO0062731 | 10/2000 |
| WO | 2007058673 | 5/2007 |
| WO | 2021176531 | 9/2021 |

OTHER PUBLICATIONS

International Search Report and Written Opinion dated Jun. 27, 2023 in PCT/IL2023/050291.

International Search Report and Written Opinion dated Jul. 20, 2023 in PCT/IB2023/054218.

* cited by examiner

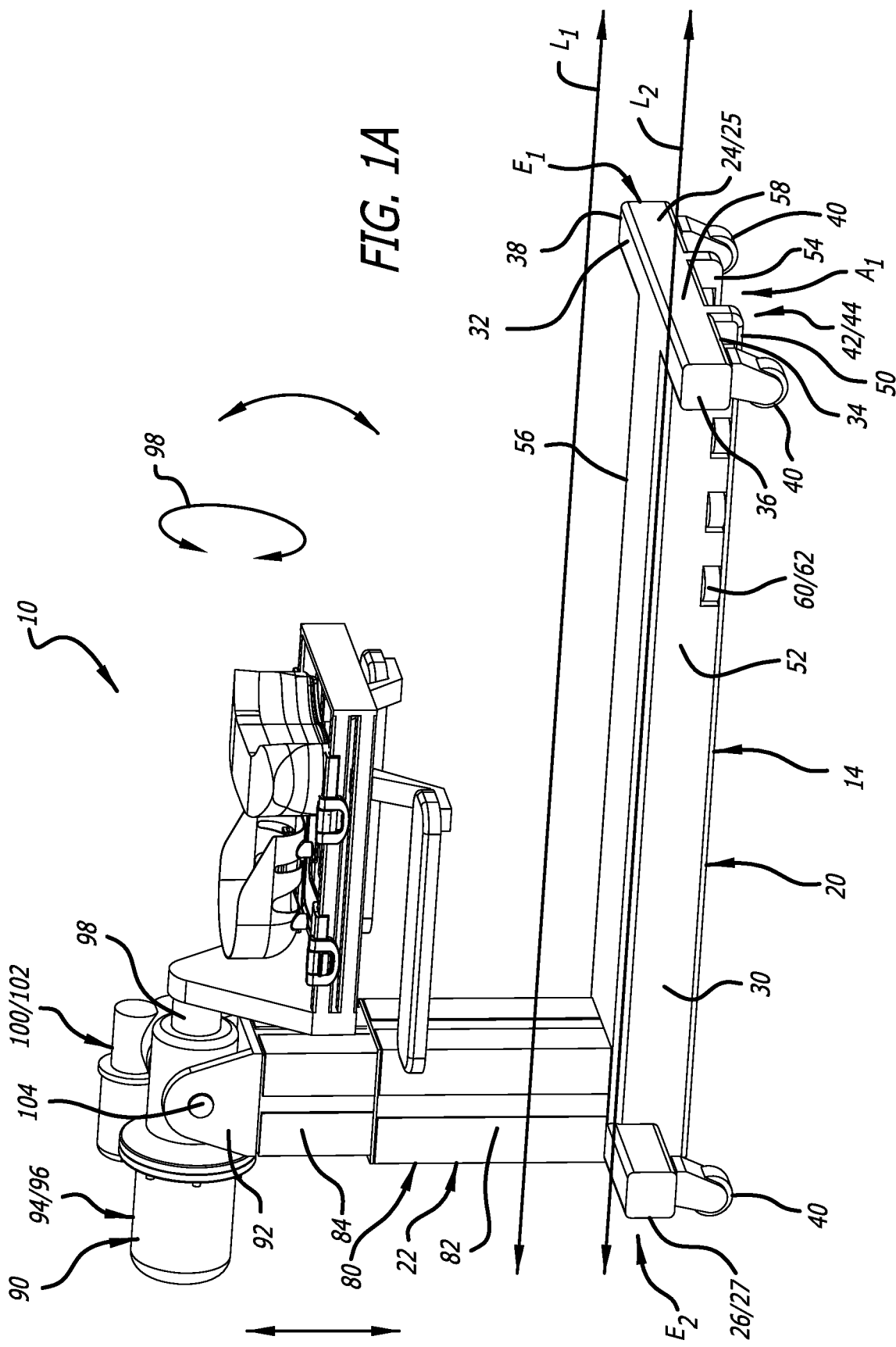

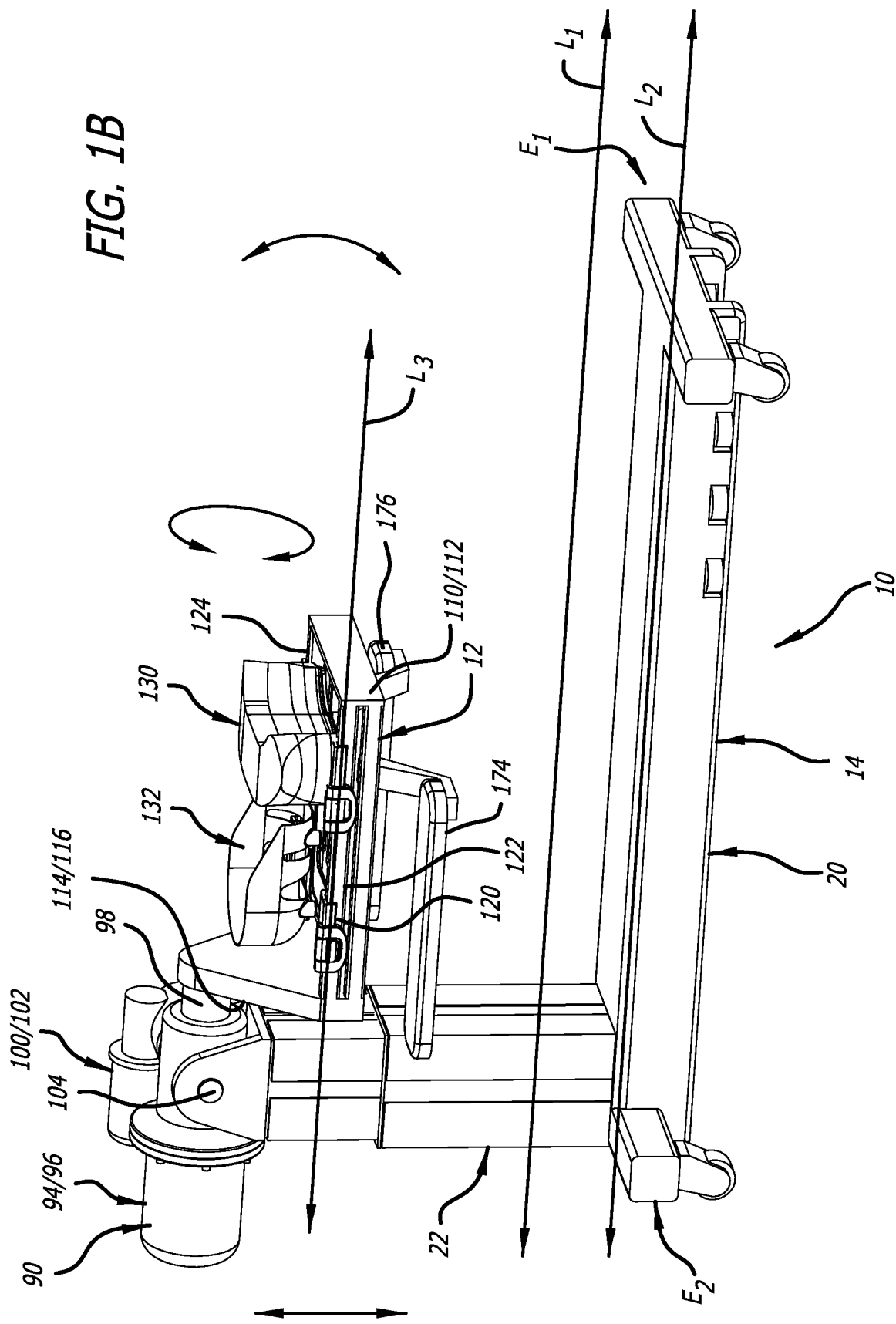

SURGICAL PLATFORM SYSTEM

FIELD

The present technology generally relates to a surgical platform system having a first platform portion and a second platform portion that can be used to adjust portions of a patient supported thereby before, during, and after surgery in relation to a surgical robotic system providing increased degrees of adjustment for at least one of the first platform portion and the second platform portion.

BACKGROUND

Typically, conventional surgical tables include some form of patient articulation, but such patient articulation afforded thereby is often quite limited. For example, sometimes the conventional surgical tables can afford a limited degree of flexion or extension of the spine of the patient by lifting a portion of the torso of the patient in a upward direction and a downward direction. The patient articulation afforded by the convention surgical tables is limited because patient platforms thereof are typically horizontally-oriented, and the patient articulation is relative to the horizontal orientations of the patient platforms. That is, adjustment mechanisms used to manipulate the patient are integrated into the horizontally-oriented patient platforms, and the limits of the corresponding adjustment is oftentimes constrained by such integration. Other types of surgical tables include patient platform portions that are attached to and articulatable with respect one another. However, patient articulation afforded by these other types of surgical tables is oftentimes constrained by the attachment of the patient platform portions to one another, and oftentimes limited to only one axis or in one plane. Therefore, in order to enhance patient articulation, there is a need for a surgical platform system including a first platform portion and a second platform portion that are separated from one another to afford independent movement therebetween. Such a surgical platform system incorporating the first platform portion and the second platform portion independently moveable with respect to one another can correspondingly position/orient and reposition/reorient a first portion of the patient's body supported by the first platform portion, and a second portion of the patient's body supported by the second platform portion, and at least one of the first platform portion and the second platform portion can have increased degrees of freedom for such positioning and orienting. Portions of the surgical platform system can be attached relative to and/or integrated with a surgical robotic system to afford positioning and repositioning the patient's body relative thereto before, during, and after surgery.

SUMMARY

The techniques of this disclosure generally relate to a surgical platform system that can be used as a surgical table for performing surgery on a patient supported thereby, with a first platform portion and a second platform portion of the surgical platform system capable of supporting a first portion and a second portion, respectively, of the patient thereon. The first platform portion and the second platform portion can be independently moveable with respect to one another, and portions of the surgical platform system can be integrated with a surgical robotic system to afford positioning/orienting and repositioning/reorienting the patient's body relative to the surgical robot before, during, and after surgery.

In one aspect, the present disclosure provides a surgical platform system including a first platform portion and a support portion supporting the first platform portion, the support portion including a first support structure, a second support structure, and an adjustment portion, the first support structure having a first end, an opposite second end, a mid-longitudinal axis extending through the first end and the second end of the first support structure, a first end portion at the first end, a second end portion at the second end, and at least one cross member extending between the first end portion and the second end portion, the second end portion including a slider portion and a rotator portion supported by the slider portion, the second support structure extending upwardly from the rotator portion of the first support structure, the second support structure vertically spacing the adjustment portion apart from the first support structure, and the adjustment portion rotatably and tiltably supporting the first platform portion relative to the first support structure and the second support structure; and the first platform portion including a first end, an opposite second end, a first end portion at the first end of the first platform portion, a second end portion at the second end of the first platform portion, at least a first rail and a second rail extending between the first end portion and the second end portion of the first platform portion, a head support, and a chest support supported by the at least the first rail and the second rail of the first platform portion; and a second platform portion including a first end, an opposite second end, a first end portion at the first end of the second platform portion, a second end portion at the second end of the second platform portion, at least a first rail and a second rail extending between the first end portion and the second end portion of the second platform portion, and at least a first thigh support and a second thigh support supported by the at least the first rail and the second rail of the second platform portion; where the support portion is positionable relative to a robotic system, and the first end portion of the second platform portion is supported relative to the robotic system; where, when the support portion is positioned relative to the robotic system, the first platform portion and the second platform portion are positioned adjacent to one another and separated by a gap between the first end of the first platform portion and the second end of the second platform portion; and where the first platform portion is moveable side-to-side across the mid-longitudinal axis via operation of the slider portion, the first platform portion is rotatable about an axis transverse to the mid-longitudinal axis via operation of the rotator portion, the first platform portion is at least one of tiltable upwardly/downwardly and rotatable about an axis aligned with the mid-longitudinal axis via operation of the adjustment portion in order to position/orient and reposition/orient a first portion of a patient supported by the first platform portion relative to a second portion of the patient supported by the second platform portion.

In another aspect, the present disclosure provides a surgical platform system including a first platform portion and a support portion, the support portion supporting the first platform portion above and vertically spacing the first platform portion apart from the ground, the support portion including an end portion including a slider portion and a rotator portion supported by the slider portion, a vertical portion extending upwardly from the rotator portion, and an adjustment portion supported by the vertical portion, the first platform portion being rotatably and tiltably connected to the adjustment portion; and the first platform portion including a first end, an opposite second end, a first end portion at the first end of the first platform portion, a second end portion at the second end of the first platform portion, at least a first rail and a second rail extending between the first end portion and the second end portion of the first platform portion, a head support, and a chest support supported by the at least the first rail and the second rail of the first platform portion; and a second platform portion including a first end, an opposite second end, a first end portion at the first end of the second platform portion, a second end portion at the second end of the second platform portion, at least a first rail and a second rail extending between the first end portion and the second end portion of the second platform portion, and at least a first thigh support and a second thigh support supported by the at least the first rail and the second rail of the second platform portion; where the support portion is positionable relative to a robotic system, and the first end portion of the second platform portion is supported relative to the robotic system; where, when the support portion is positioned relative to the robotic system, the first platform portion and the second platform portion are positioned adjacent to one another and separated by a gap between the first end of the first platform portion and the second end of the second platform portion; and where the first platform portion is moveable side-to-side via operation of the slider portion, the first platform portion is rotatable about an axis transverse to the mid-longitudinal axis via operation of the rotator portion, the first platform portion is at least one of tiltable upwardly/downwardly and rotatable via operation of the adjustment portion in order to position/orient and reposition/reorient a first portion of a patient supported by the first platform portion relative to a second portion of the patient supported by the second platform portion.

In yet another aspect, the present disclosure provides a surgical platform system including a first platform portion and a support portion supporting the first platform portion, the support portion including a first support structure, a second support structure, and an adjustment portion, the first support structure having a first end, an opposite second end, a mid-longitudinal axis extending through the first end and the second end of the first support structure, a first end portion at the first end, a second end portion at the second end, and at least one cross member extending between the first end portion and the second end portion, the second end portion including a slider portion and a rotator portion supported by the slider portion, the second support structure extending upwardly from the rotator portion of the first support structure, the second support structure vertically spacing the adjustment portion apart from the first support structure, and the adjustment portion rotatably and tiltably supporting the first platform portion relative to the first support structure and the second support structure; and the first platform portion including a first end, an opposite second end, and a length between the first end and the second end of the first platform portion, the first platform portion being configured to support a first portion of a patient thereon; and a second platform portion including a first end, an opposite second end, and a length between the first end and the second end of the second platform portion, the second platform portion being configured to support a second portion of a patient thereon; where, when the support portion is positioned relative to the robotic system, the first platform portion and the second platform portion are positioned adjacent to one another and separated by a gap between the first end of the first platform portion and the second end of the second platform portion; and where the first platform portion is moveable side-to-side across the mid-longitudinal axis via operation of the slider portion, the first platform portion is rotatable about an axis transverse to the mid-longitudinal axis via operation of the rotator portion, the first platform portion is at least one of tiltable upwardly/downwardly and rotatable about an axis aligned with the mid-longitudinal axis via operation of the adjustment portion in order to position/orient and reposition/reorient the portions of a patient supported by the first platform portion and the second platform portion relative to one another.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The techniques of this disclosure generally relate to a surgical platform system.

FIG. 1A is a side, perspective view that illustrates a first portion of a surgical platform system of the present disclosure;

FIG. 1B is a side, perspective view similar to FIG. 1A that illustrates the first portion of the surgical platform system;

Figure 3:
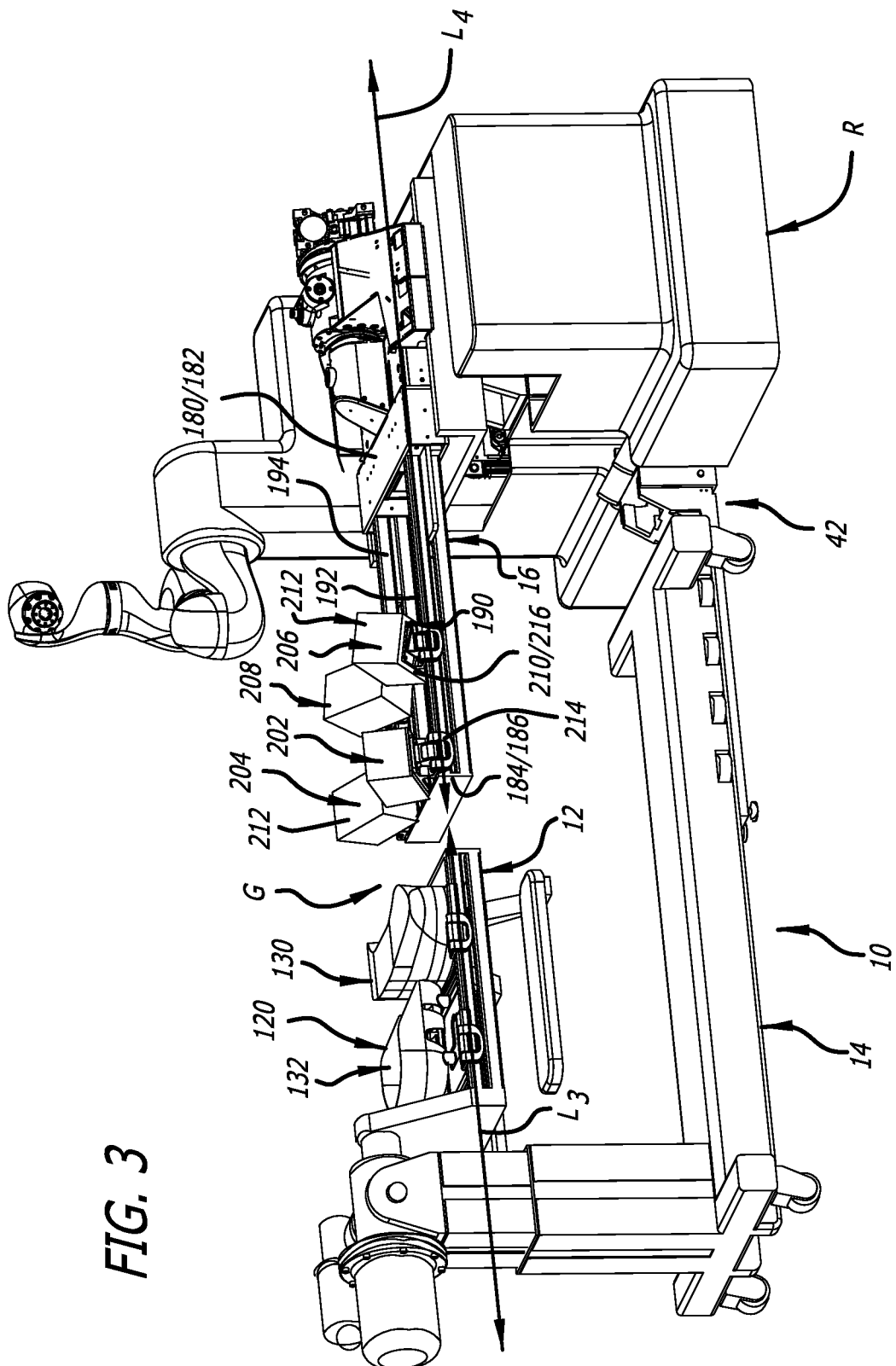
FIG. 3 is a side, perspective view that illustrates the first portion of the surgical platform system of FIG. 1A in position relative to the second portion of the surgical platform system and the surgical robotic system supporting the second portion of the surgical platform system of FIG. 2.
Figure 4:
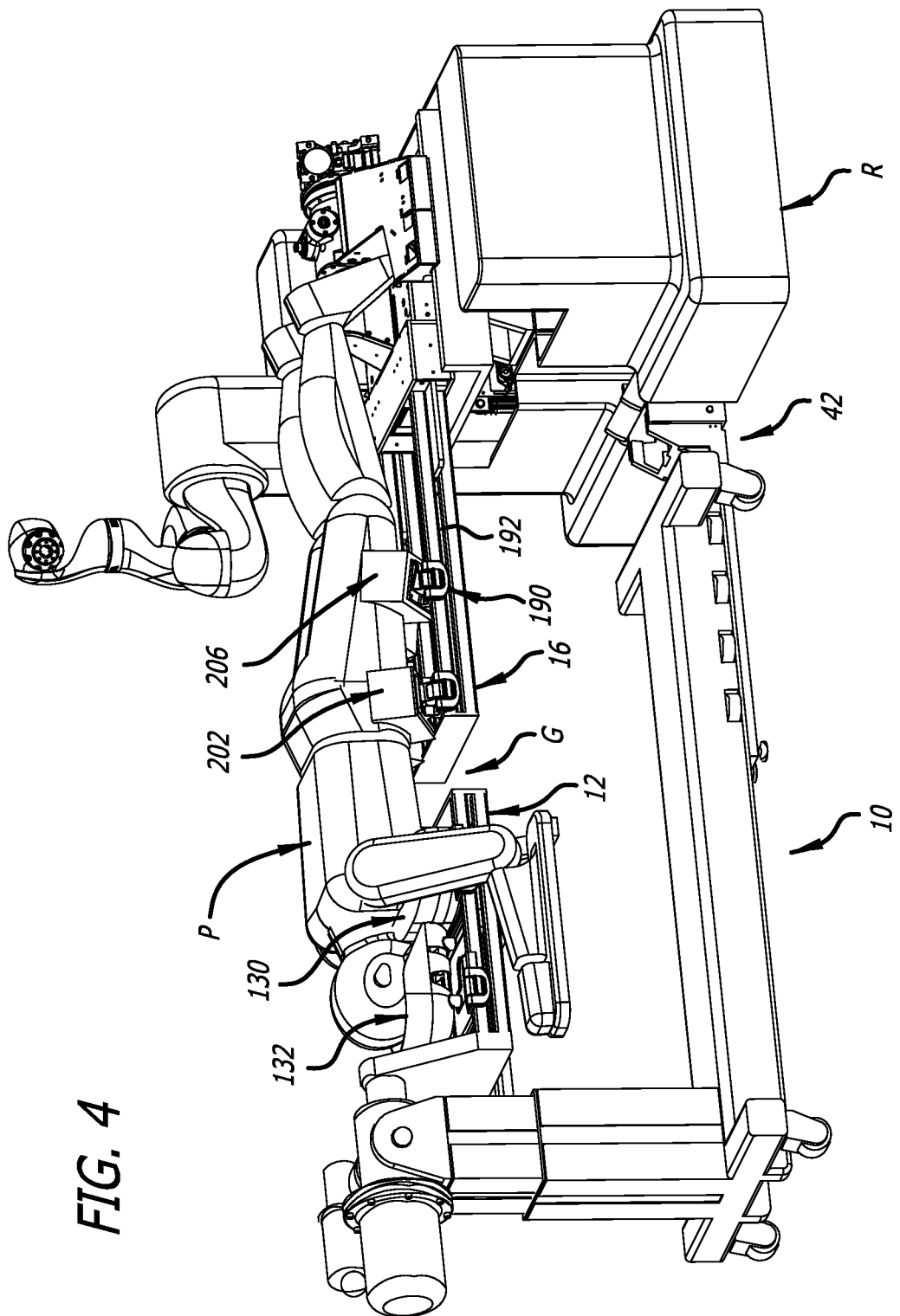
FIG. 4 is a side, perspective view that illustrates a patient supported on the first and second portions of the surgical platform system in a prone position with the first and second portions of the surgical platform system positioned relative to one another as depicted in FIG. 3.
Figure 5:
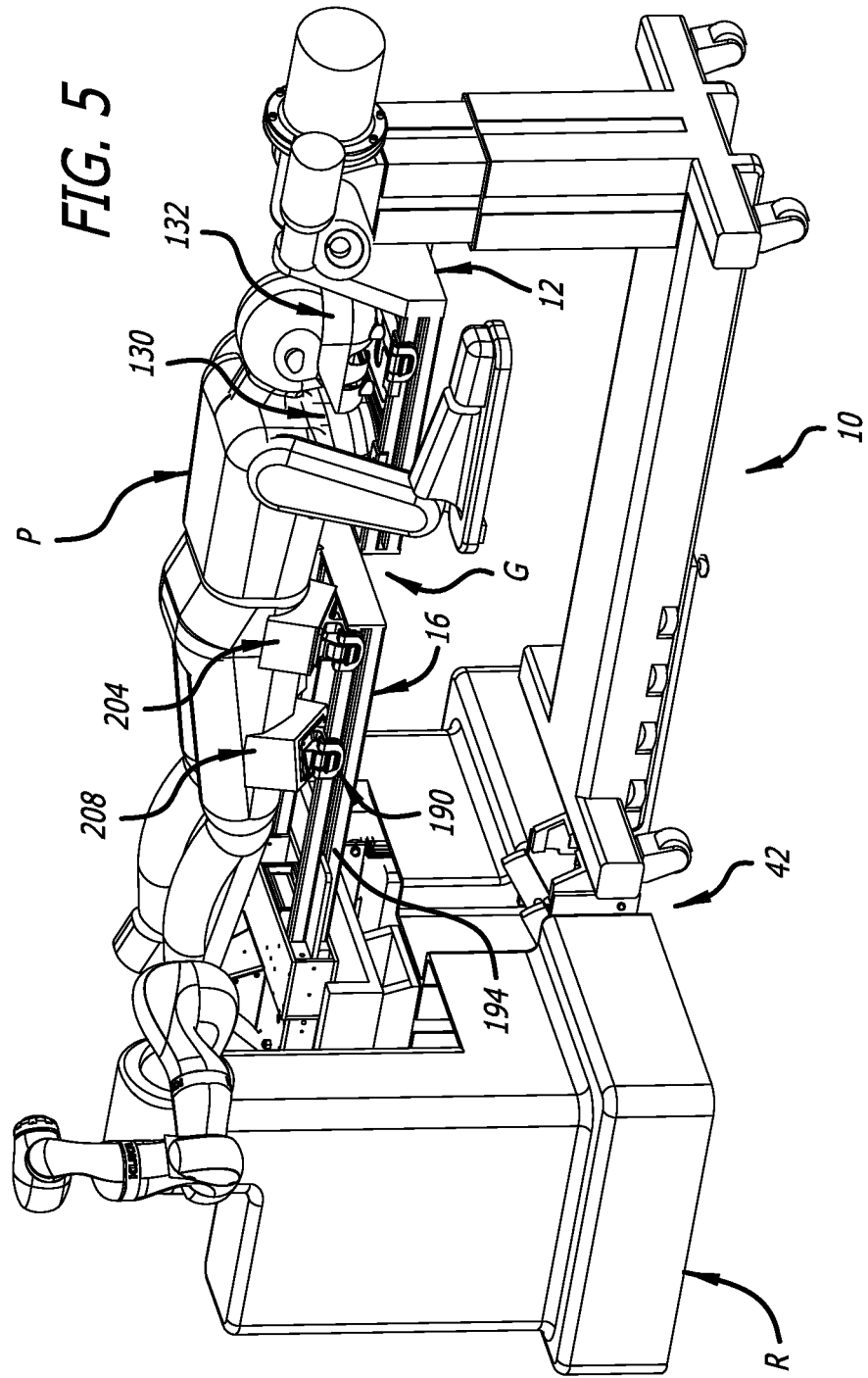
FIG. 5 is another side, perspective view that illustrates the patient supported on the first and second portions of the surgical platform system in a prone position with the first and second portions of the surgical platform system positioned relative to one another as depicted in FIG. 3.
Figure 6:
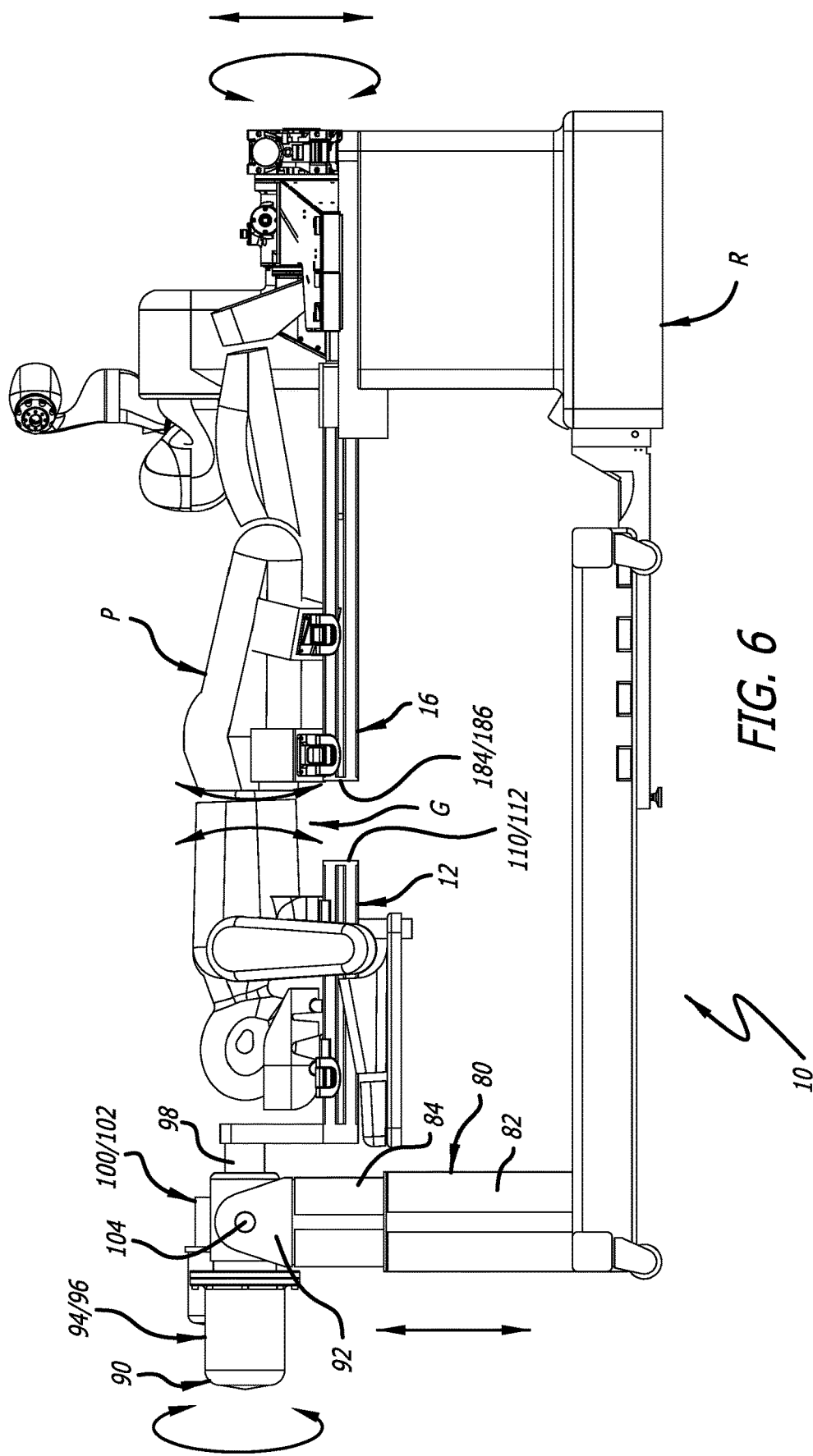
FIG. 6 is a side, elevational view that illustrates the patient supported on the first and second portions of the surgical platform system in a prone position with the first and second portions of the surgical platform system positioned relative to one another as depicted in FIG. 3.
Figure 10:
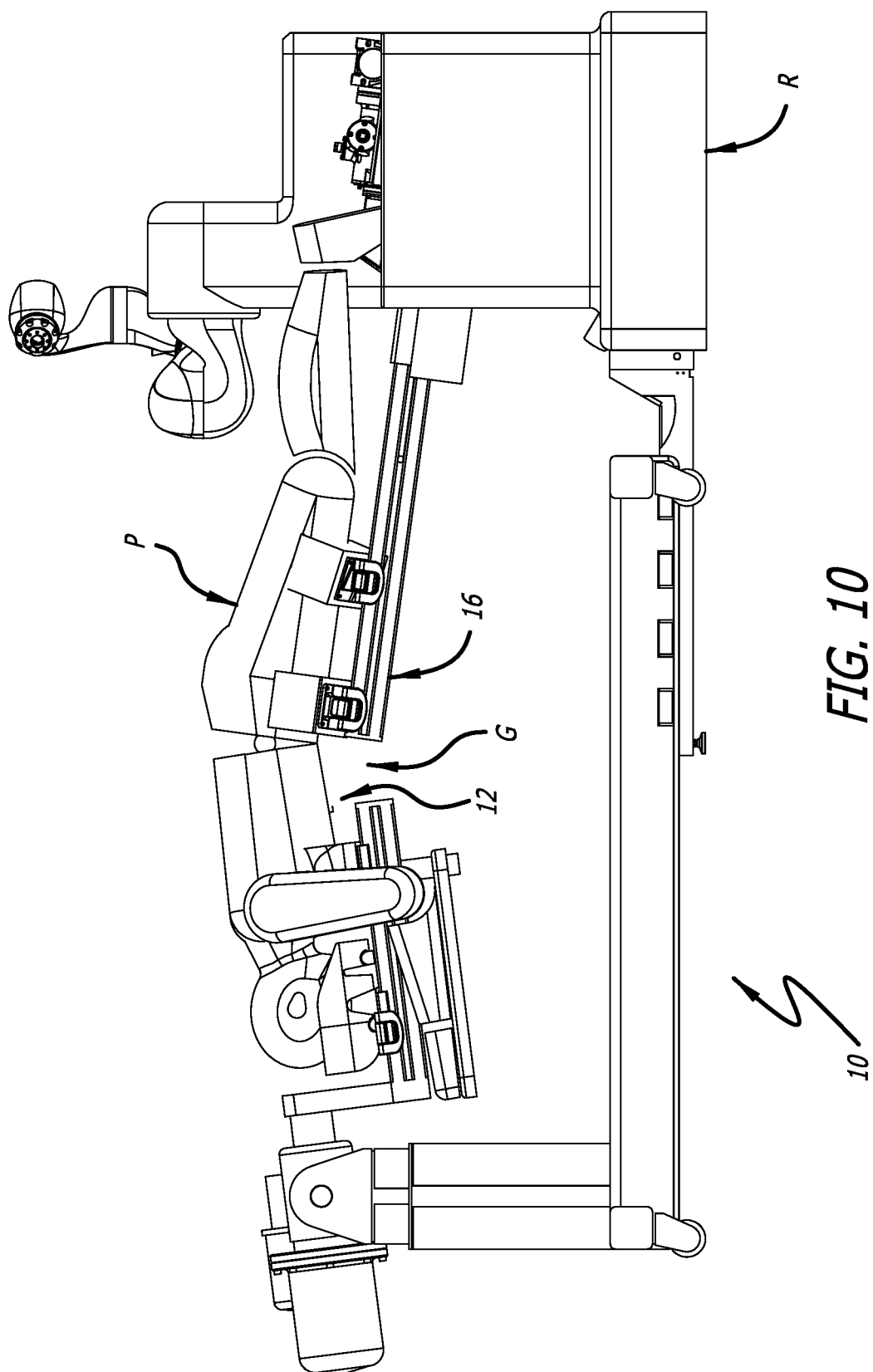
Figure 11:
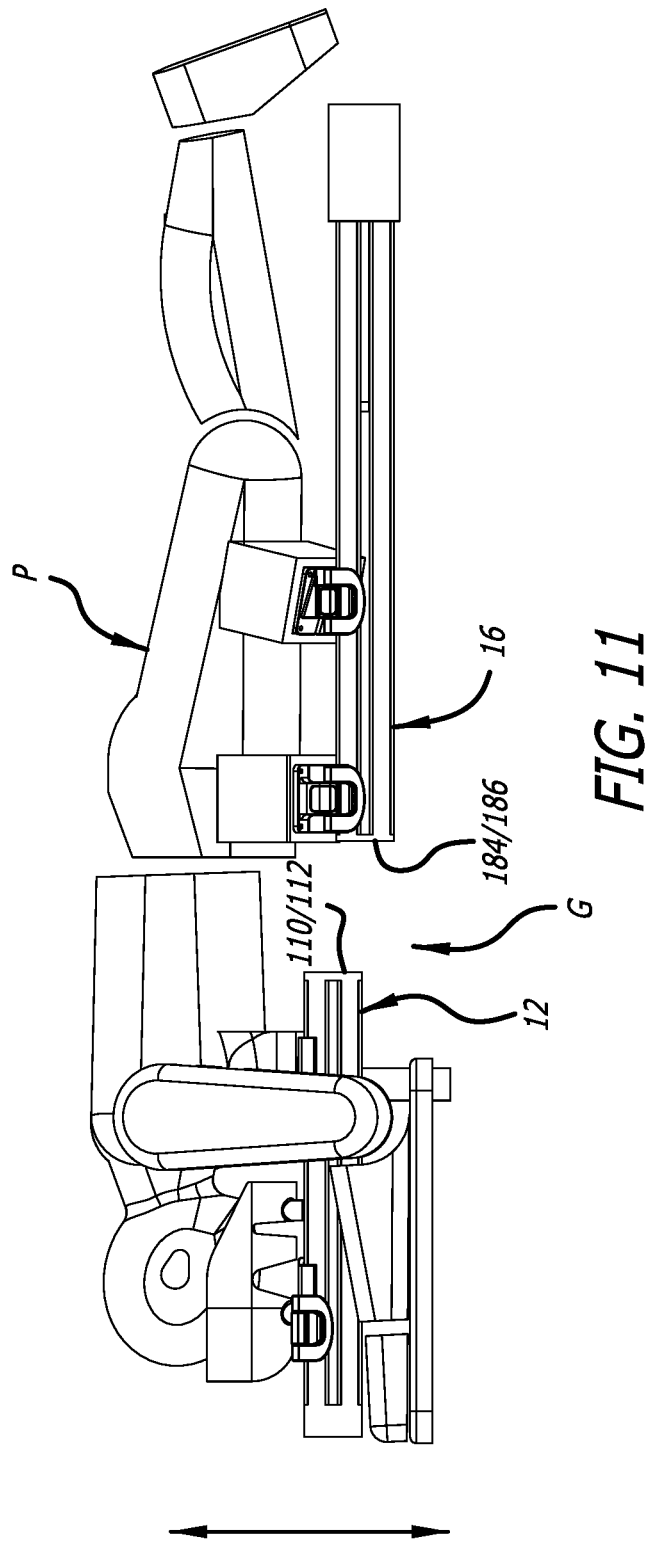
Figure 12:
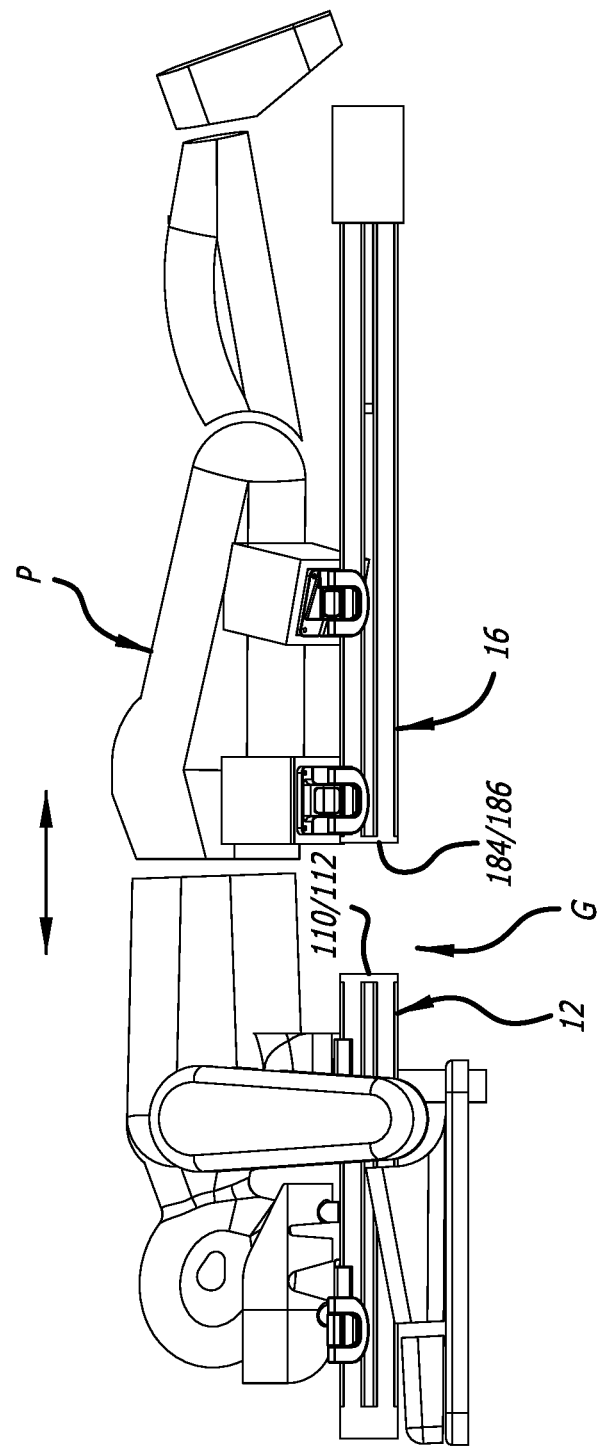
Figure 13:
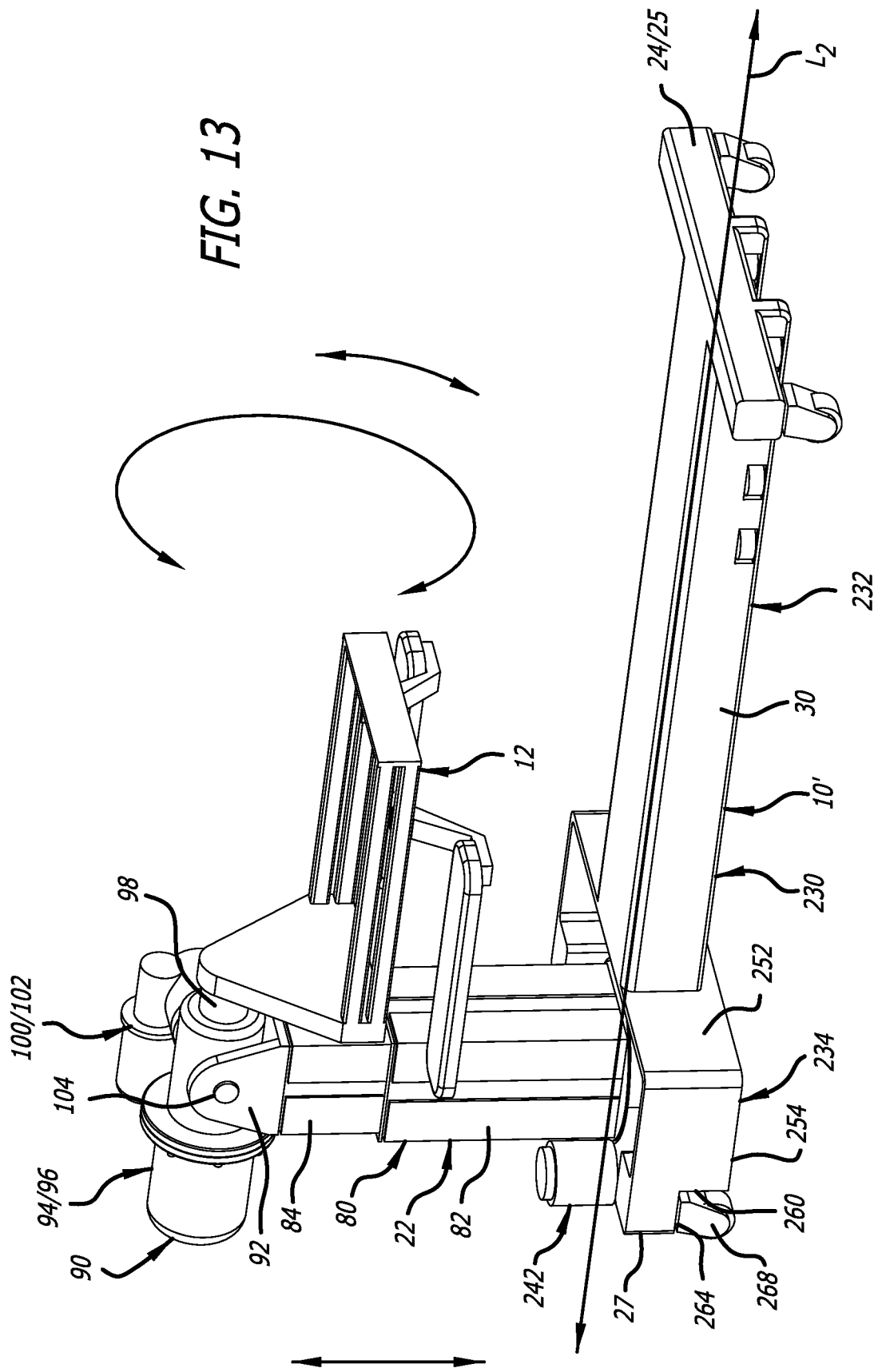
Figure 14:
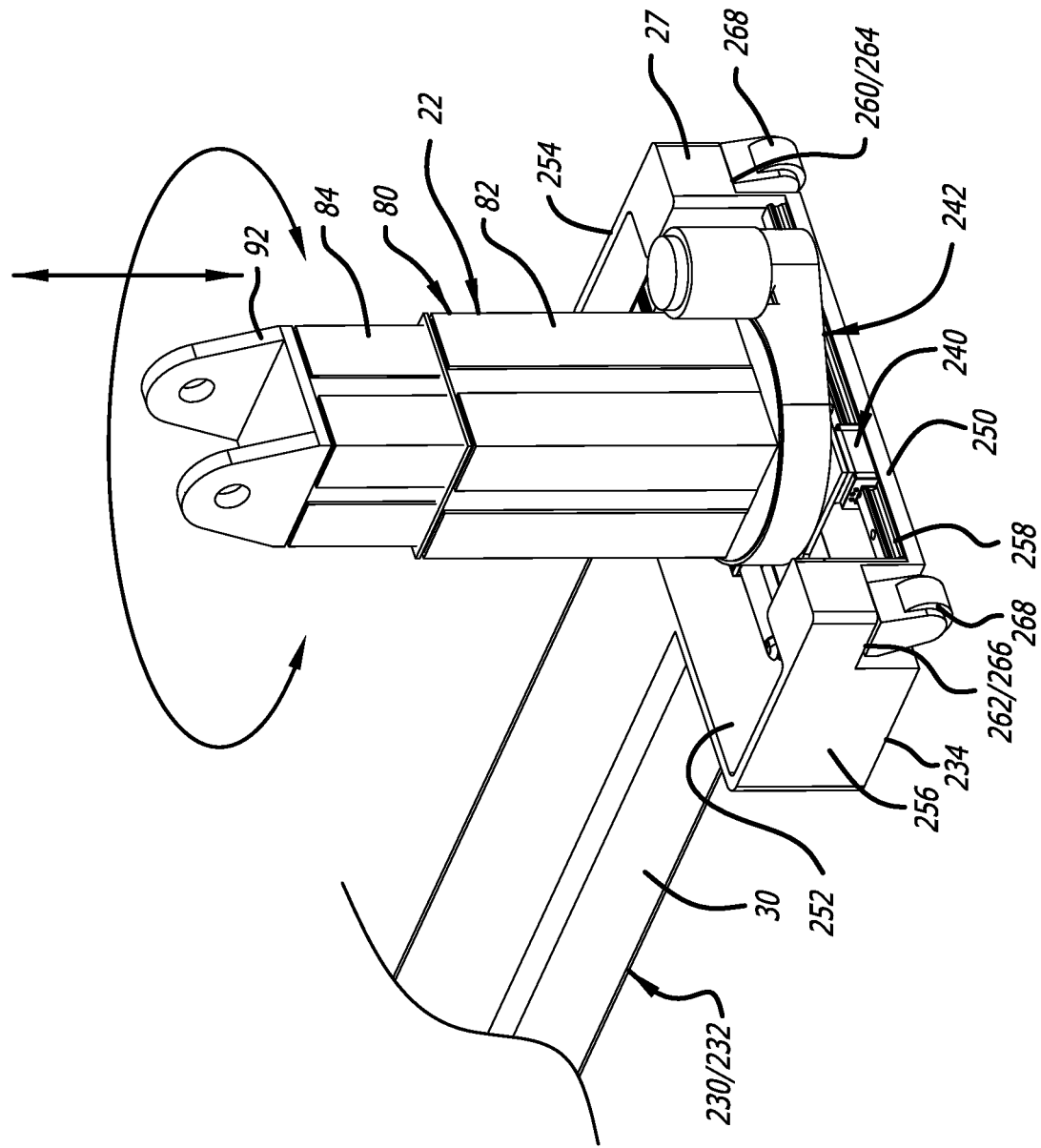
Figure 15:
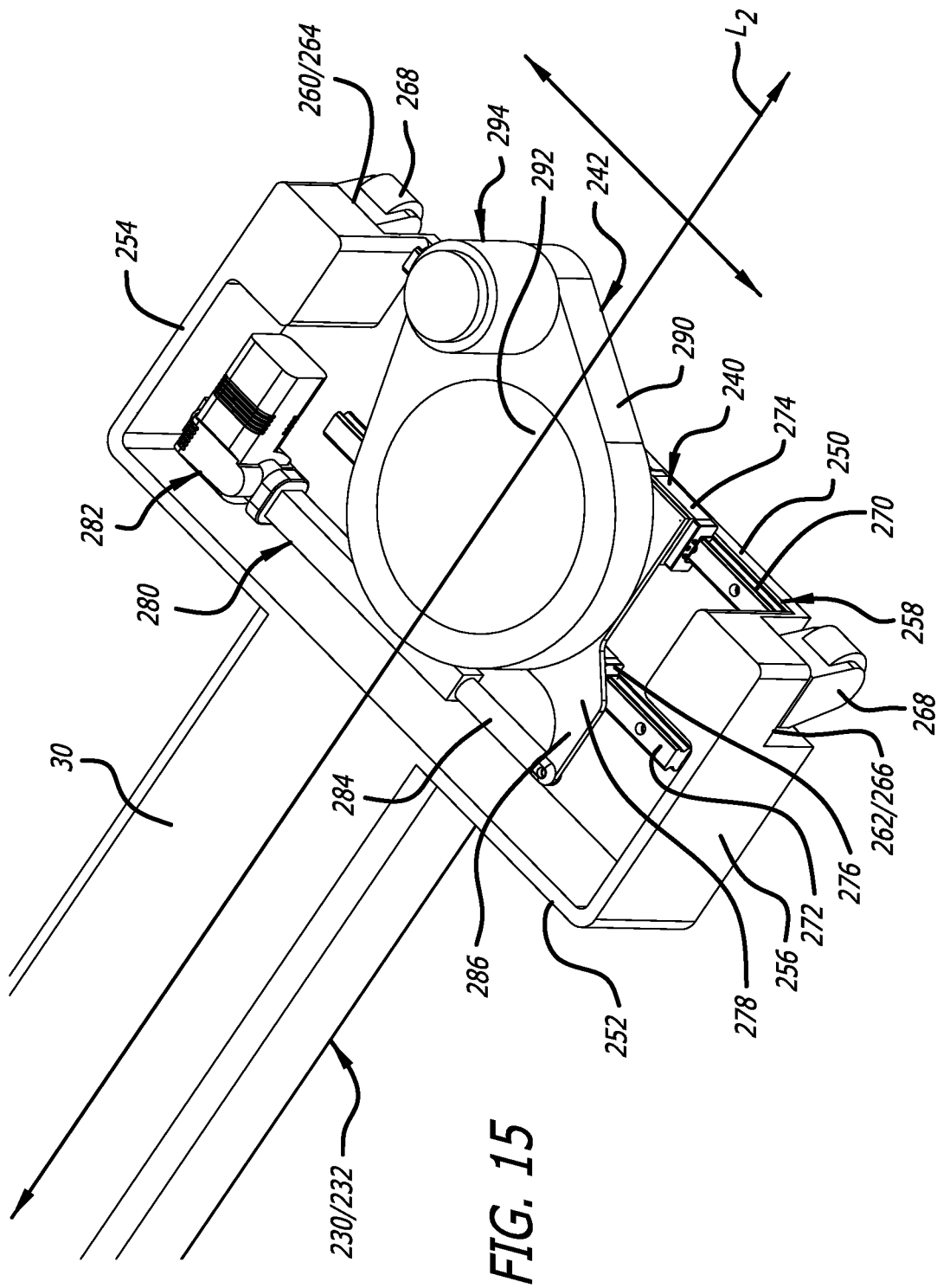
Figure 16:
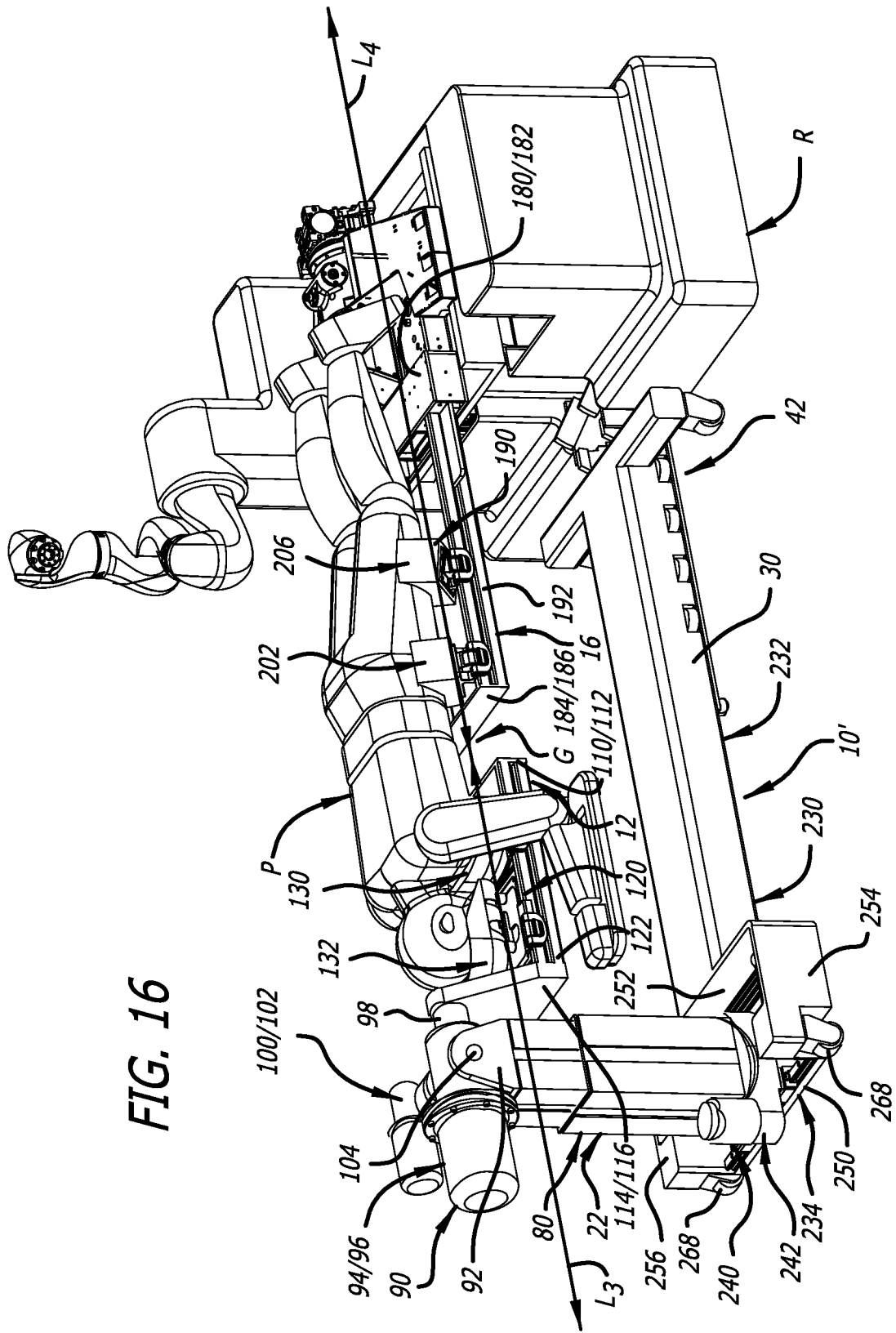
Figure 17:
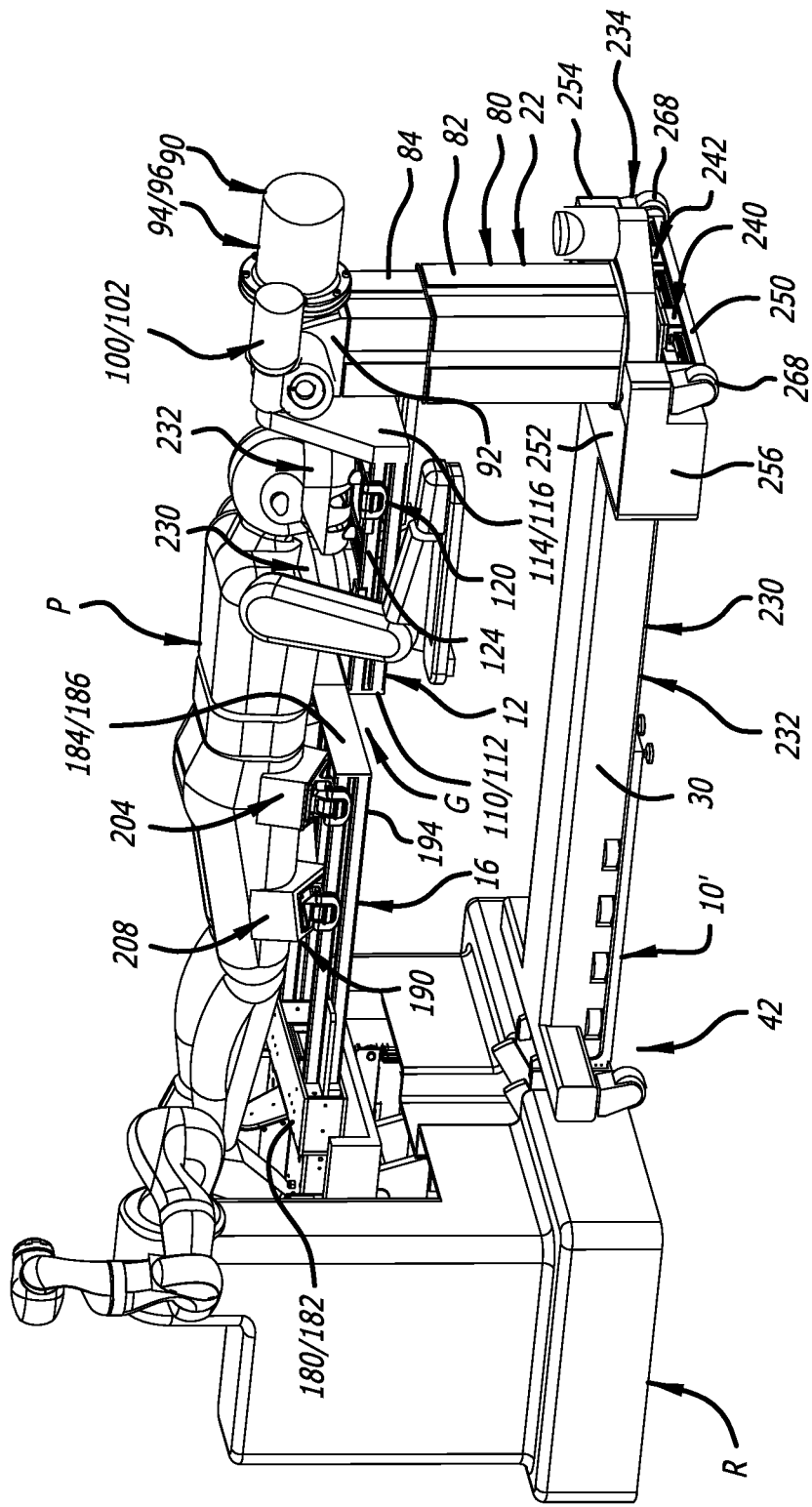
Figure 18:
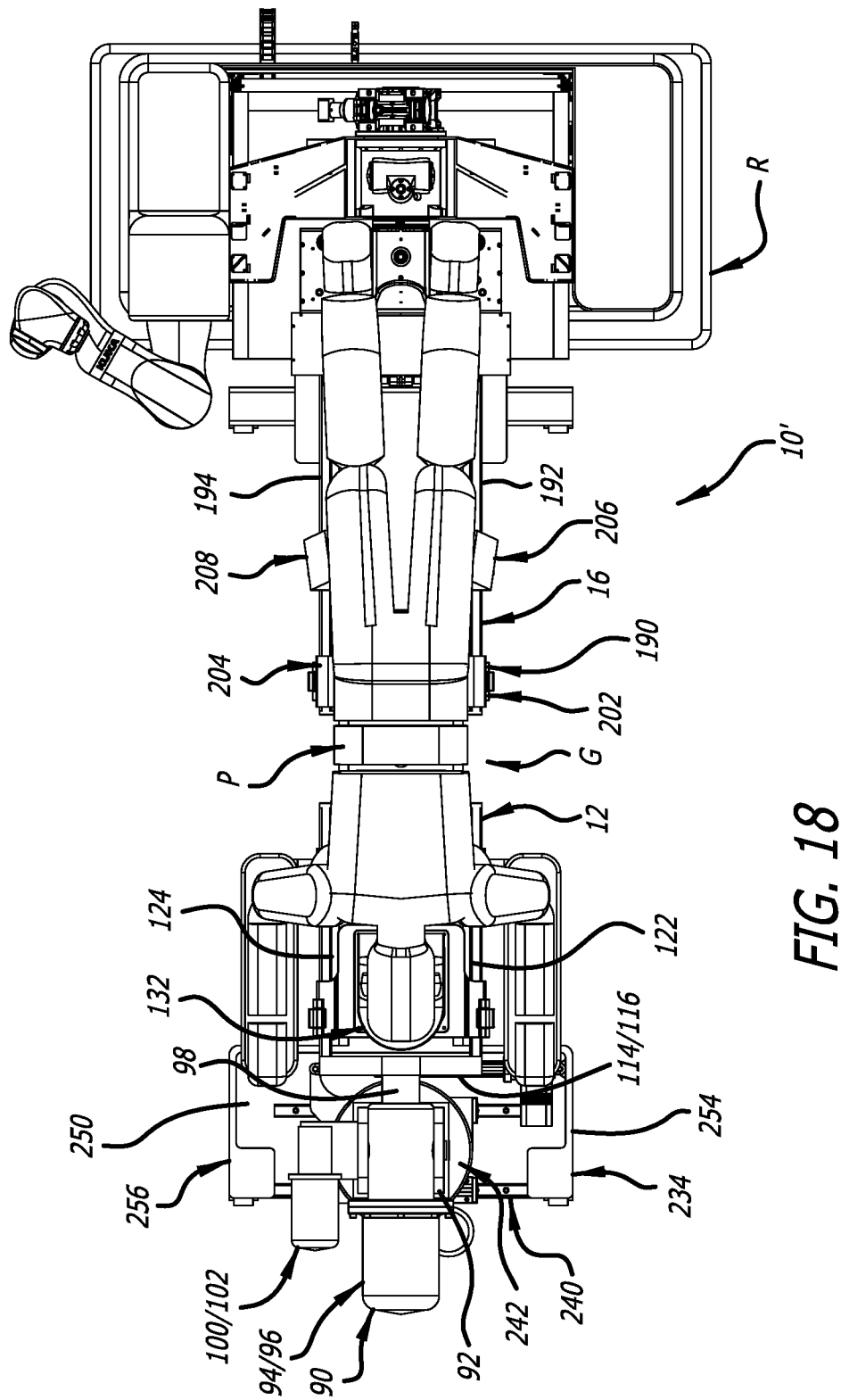
Figure 19:
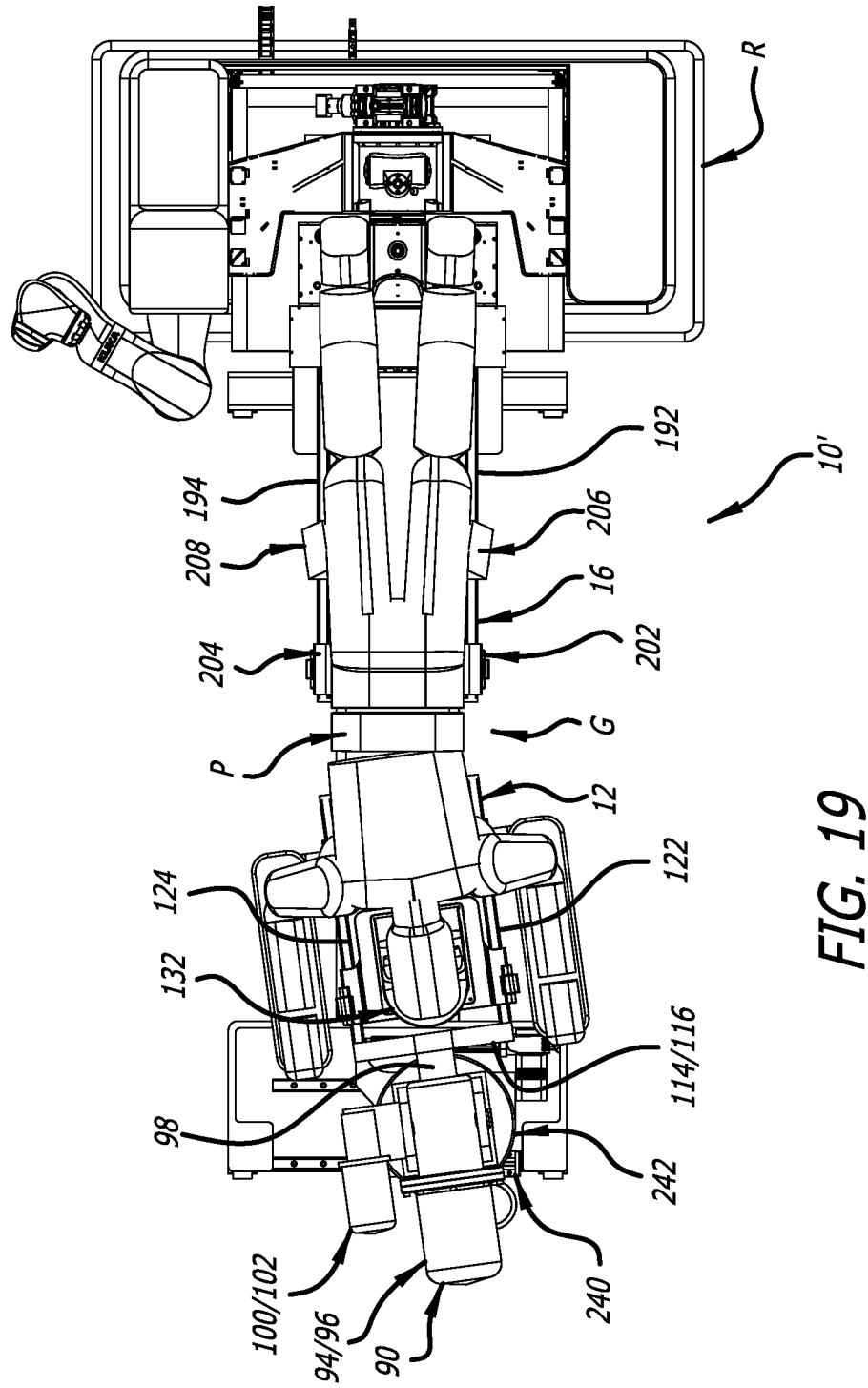
Figure 20:
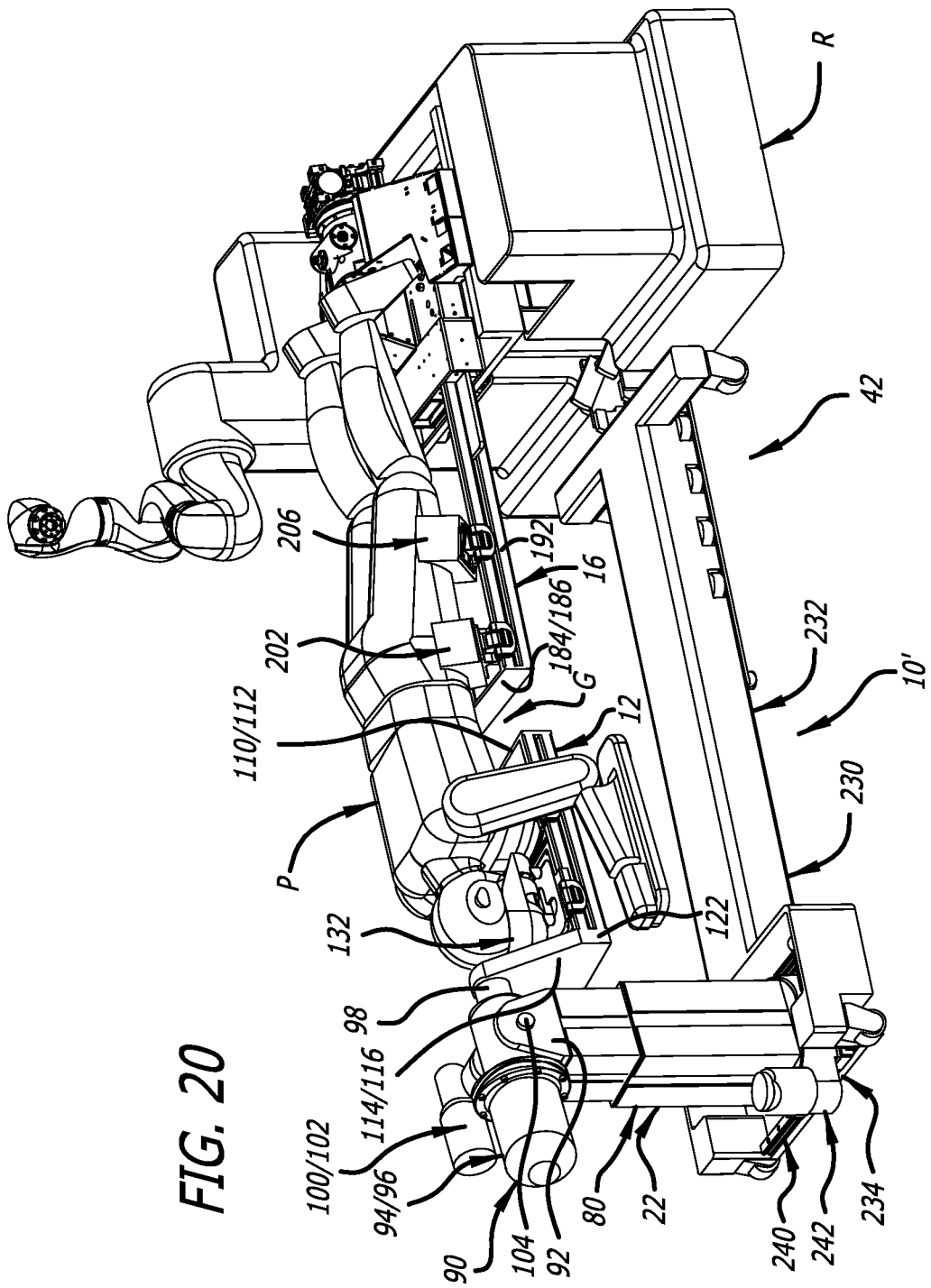
Figure 21:
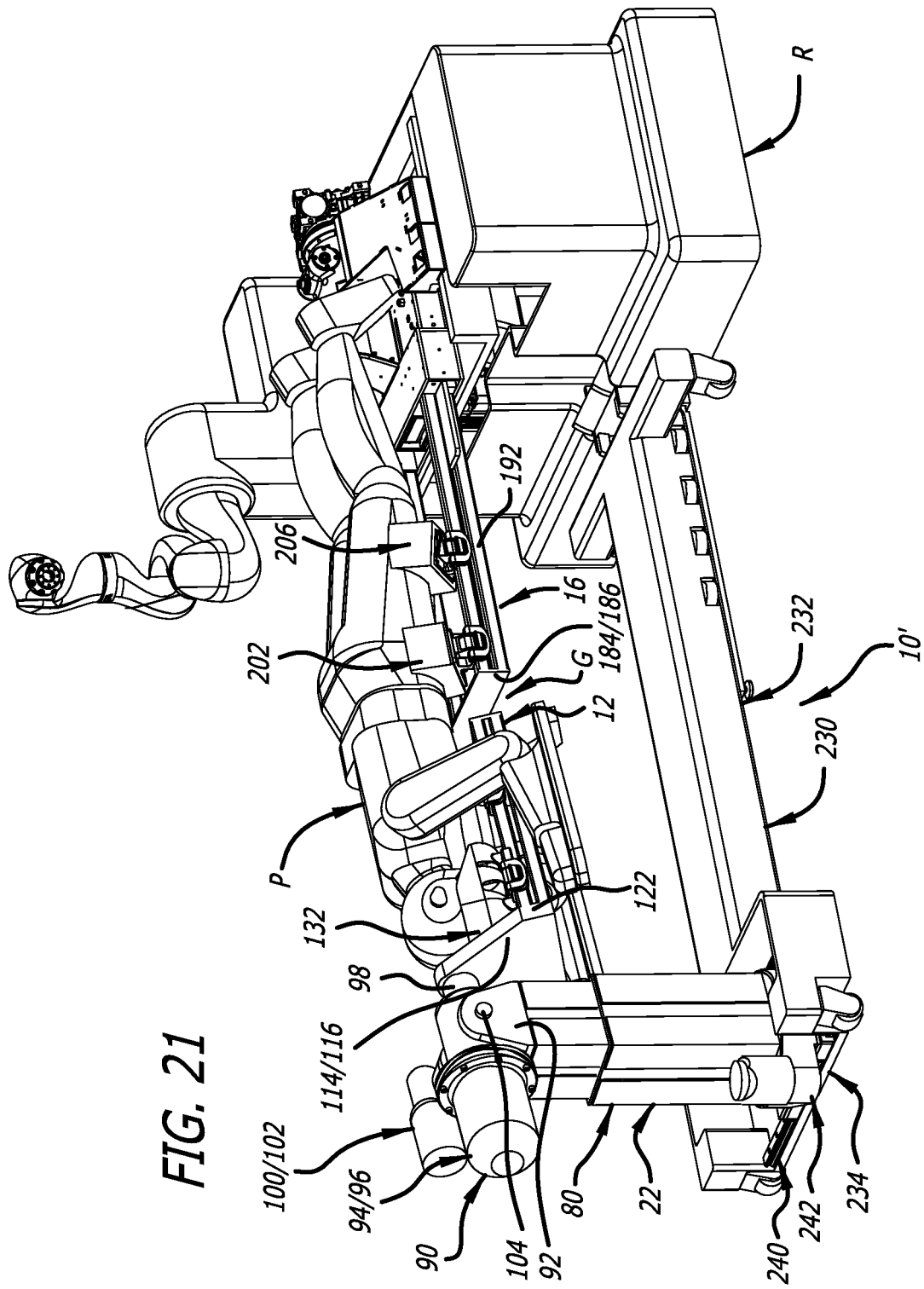

1A and the corresponding first and second portions of the patient supported thereon raised and tilted downwardly relative to another;

FIG. 10 is a side, elevational view that illustrates the first and second portions of the surgical platform system of FIGS. 1A and 3 and the corresponding first and second portions of the patient supported thereon lowered and tilted upwardly relative to another;

FIG. 11 is a side, elevational view that illustrates the first portion of the surgical platform system and the first position of the patient positioned thereon raised relative to the second portion of the surgical platform system and the second portion of the patient positioned thereon;

FIG. 12 is a side, elevational view that illustrates the first and second portions of the surgical platform system and the corresponding first and second portions of the patient supported thereon positioned further apart from one another;

FIG. 13 is a side, perspective view that illustrates a first portion of a modified surgical platform system of the present disclosure;

FIG. 14 is an end, perspective view that illustrates a slider portion and a rotator portion of the first portion of the modified surgical platform system of FIG. 13;

FIG. 15 is a top, perspective view that illustrates the slider portion and the rotator portion of the first portion of the modified surgical platform system of FIG. 13;

FIG. 16 is a side, perspective view that illustrates the first portion of the modified surgical platform system of FIG. 13 in position relative to a second portion of the modified surgical platform system and a surgical robotic system supporting the second portion of the modified surgical platform system with the patient supported by the first and second portions of the modified surgical platform system in a prone position;

FIG. 17 is another side, perspective view that illustrates the patient supported by the first and second portions of the modified surgical platform system with the patient in the prone position;

FIG. 18 is a top, plan view that illustrates the patient supported by the first and second portions of the modified surgical platform system with the patient in the prone position;

FIG. 19 is a top, plan view that illustrates the patient supported by the first and second portions of the modified surgical platform system with the sagittal position of the patient adjusted via relative adjustment of the first portion with respect to the second portion of the modified surgical platform system;

FIG. 20 is a side, perspective view that illustrates the patient supported by the first and second portions of the modified surgical platform system with the sagittal position of the patient adjusted via relative adjustment of the first portion with respect to the second portion of the modified surgical platform system; and FIG. 21 is side, perspective view that illustrates the patient supported by the first and second portions of the modified surgical platform system with the sagittal and torsional position of the patient adjusted via relative adjustment of the first portion with respect to the second portion of the modified surgical platform system.

DETAILED DESCRIPTION

A preferred embodiment of a surgical platform system of the present disclosure is generally indicated by the numeral 10' in FIGS. 13 and 16-21. The surgical platform system 10' is a modified version of, and thus, is similar to and includes many features of a surgical platform system 10 introduced in FIGS. 1-10. As discussed below, the modified surgical platform system 10' affords additional movement and manipulation of a patient P in comparison to the surgical platform system 10.

As depicted in FIG. 1A, the surgical platform system 10 includes a first end $E_1$, a second end $E_2$, and a mid-longitudinal $L_1$ extending through the first end $E_1$ and the second end $E_2$. The surgical platform system 10 includes a first platform portion 12 and a support portion 14. The support portion 14 supports the first platform portion 12, and the first platform portion 12 can support a portion of a patient P thereon. The first platform portion 12 and the support portion 14 can be positioned and repositioned relative to and used in association with a surgical robotic system or robotic surgical guidance system (hereinafter referred to as "robotic system") generally indicated by the letter R (FIGS. 2-10).

The surgical platform system 10 can include a second platform portion 16 attached relative to or integrated with the robotic system R for supporting a portion of the patient P different than that supported by the first platform portion 12. A gap G is provided between the first platform portion 12 and the second platform portion 16. Together, when the patient P is supported thereby, adjustment of the first platform portion 12 and the second platform portion 16 via independent movement relative to one another can be used to manipulate and provide access to portions of the body of patient P. In doing so, the independent adjustment of the first platform portion 12 and the second platform portion 16 relative to another can be used to position/orient and reposition/reorient portions of the patient supported thereby. The surgical platform system 10 and/or the robotic system R can include a controller or controllers for controlling motorized actuators included in the surgical platform system 10 to facilitate the operation thereof. In some embodiments, for example, one of more controllers of the surgical platform system 10 and/or the robotic system R can coordinate movement therebetween by moving the first platform portion 12 and the second platform portion 16 relative to one another. And the robotic system R can be used for performing surgery or facilitating performance of surgery, and such surgery, for example, can included spinal surgery on the spine of the patient P.

During use, the support portion 14 can be used to facilitate movement of the first platform portion 12, and can be used positioning the first platform portion 12 relative to the robotic system R. The support portion 14, as depicted in FIGS. 1 and 2, includes a horizontally-oriented portion 20 and a vertically-oriented portion 22. The horizontally-oriented portion 20 is used in supporting the vertically-oriented portion 22 relative to the ground, and the vertically-oriented portion 22 is used in supporting the first platform portion 12 relative to the horizontally-oriented portion 20. After being properly positioned relative to the robotic system R, the support portion 14 can be interconnected with the robotic system R by attachment of a portion of the horizontally-oriented portion 20 to a portion of the robotic system R.

As depicted in FIGS. 1A and 1B, the horizontally-oriented portion 20 includes a first end member 24 at a first end 25 thereof (collocated with the first end $E_1$), a second end member 26 at a second end 27 thereof (collocated with the second end $E_2$), and a cross member 30 extending between the first end member 24 and the second end member 26. The cross member 30 can be aligned with a mid-longitudinal axis $L_2$ of the horizontally-oriented portion 20, can be used to connect the first end member 24 and the second end member 26, and can be expandable and contractable to expand and contract a length of the horizontally-oriented portion 20 along the mid-longitudinal axis $L_2$. Each of the first end member 24 and the second end member 26 includes an upper surface 32, a lower surface 34, a first lateral end 36, and a second lateral end 38. Furthermore, casters 40 can be attached relative to the lower surfaces 34 adjacent the first lateral ends 36 and the second lateral ends 38 of the of the first end member 24 and the second end member 26 to space the first end member 24 and the second end member 26 from the ground and to facilitate movement of the support portion 14.

The surgical platform system 10 initially can be positioned relative to the robotic system R using a positioner 42 having portions provided as part of the surgical platform system 10 and the robotic system R. To illustrate, the positioner 42 can include a receiver portion 44 (FIG. 1A) that can be provided as part of the support portion 14, and a tongue portion 46 (FIG. 2) that can be attached to or positioned relative to the robotic system R, or vice versa. The receiver portion 44 can be provided at and adjacent the first end 25, can be formed by and/or attached relative to portions of the first end member 24 and the cross member 30. As depicted in FIG. 1, the receiver portion 44 is formed as a tunnel formed in portions of the first end member 24 and the cross member 30. The receiver portion 44 includes a first sidewall portion 50 with portions provided adjacent a first lateral side 52 of the cross member 30, a second sidewall portion 54 with portions provided adjacent a second lateral side 56 of the cross member 30, and an upper wall portion 58 formed in part by the lower surface 34 of the first end member 24 and portions of the cross member 30.

Portions of the first sidewall portion 50, the second sidewall portion 54, and the upper wall portion 58 form the tunnel to define a receiving area $A_1$ for receiving the tongue portion 46. Furthermore, each of the first sidewall portion 50 and the second sidewall portion 54 can include various apertures 60 adjacent the receiving area $A_1$ that are spaced therealong, and include various bumper wheels 62 rotatably mounted in the various apertures 60. Portions of the bumper wheels 62 can extend into the receiving area $A_1$. When the tongue portion 46 is received in the receiving area $A_1$, the bumper wheels 62 are used to both guide and position the tongue 46 relative the first sidewall portion 50 and the second sidewall portion 54 (and the remainder of the horizontally-oriented portion 20).

The tongue portion 46 can be attached to (FIG. 2) or otherwise positioned relative to the robotic system R, and includes a first end 64 and an opposite second end 66. The tongue portion 46 can be attached to the robotic system R at and adjacent the first end 64. Furthermore, the tongue portion 46 can include a first lateral side surface 70, a second lateral side surface 72, and a bottom surface 74 extending between the first end 64 and the second end 66. Adjustable feet 76 can be attached to the bottom surface 74 adjacent the second end 66 to facilitate leveling of at least portions of the tongue portion 46.

As depicted in FIG. 2, to initially position the support portion 14 (and the first platform portion 12 attached thereto) relative to the robotic system R, the horizontally-oriented portion 20 of the support portion 14 can be positioned so that the tongue portion 46 is received in the receiver portion 44. In doing so, the tongue portion 46 is inserted between the first sidewall portion 50 and the second sidewall portion 54, under the upper wall portion 58, and into the receiving area $A_1$. As the tongue portion 46 is received in the receiving area $A_1$, the first lateral side surface 70 contacts the bumper wheels 62 rotatably mounted to the first sidewall portion 50, and the second lateral side surface 72 contacts the bumper wheels 62 rotatably mounted to the second sidewall portion 54. Such contact affords relative movement of the tongue portion 46 to the receiver portion 44 that guides the tongue portion 46 into the receiving area $A_1$ to initially position the surgical platform system 10 relative to the robotic system R. Varying the amount of insertion of the tongue portion 46 into the receiving area $A_1$ can be used to accommodate patient's having different heights, and a locking mechanism (not shown) can be used to maintain the position of the tongue portion 46 in the receiving area $A_1$. Rather than using the positioner 42, however, an automatic interconnection mechanism (not shown) can be used to position the support portion 14 and the robotic system R relative to one another.

As depicted in FIG. 1A, the vertically-oriented portion 22 includes a telescoping column 80 for orienting and reorienting the first platform portion 12 relative to the horizontally-oriented portion 20. The telescoping column 80 includes a lower portion 82 and an upper portion 84. The lower portion of the telescoping column 80 is supported by the second end member 26 and the cross member 30, and the upper portion 84 can be telescopically moved upwardly and downwardly relative to the lower portion 82. The telescopic expansion and contraction of the telescoping column 80 can be used to correspondingly raise and lower the first platform portion 12 relative to the horizontally-oriented portion 20 to position/orient and reposition/reorient the first platform portion 12 between a lower position and an upper position.

The vertically-oriented portion 22 also includes an adjustment portion in the form of a rotational and/or tilt positioner 90. The rotational/tilt positioner 90 is supported relative to the telescoping column 80 by a clevis 92 attached to the upper portion 84. The rotational/tilt positioner 90 includes a rotational portion 94 including an actuator, in the form of a motor and transmission portion 96, and an axle 98, and a tilt portion 100 including an actuator, in the form of a motor and transmission portion 102, and an axle 104. As depicted in FIGS. 1 and 2, portions of the motor and transmission portion 96 of the rotational portion 94 can be positioned between portions of the clevis 92, and the axle 98 can extend outwardly from the motor and transmission 96 portion and be attached to the first platform portion 12. Furthermore, the motor and transmission portion 102 of the tilt portion 100 can be positioned on one side of a portion of the clevis 92, and the axle 104 can be received through the clevis 92 and be attached to portions of the rotational portion 92. Operation of the motor and transmission portion 96 serves in rotating the axle 98 to rotate the support platform 12 attached thereto, and operation of the motor and transmission portion 102 serves in rotating the axle 104 to tilt the rotational portion 92 and the support platform 12 attached thereto.

Accordingly, to position/orient and reposition/reorient the first platform portion 12, the first platform portion 12 can be raised and lowered via expansion and contraction of the telescoping column 80; the first platform portion 12 can be rotated side to side by rotation of the axle 98 (about the axis of rotation thereof) using the motor and transmission portion 96, and the first platform portion 12 can be tilted upwardly or downwardly by rotation of the axle 104 (about the axis of rotation thereof) using the motor and transmission portion 102. As such, the rotation of the axle 98 rotates the first platform portion 12 side to side in a vertical plane perpendicular to the mid-longitudinal axes $L_1$ and $L_2$, and the rotation of the axle 104 tilts the first platform portion 12 upwardly and downwardly in a vertical plane aligned with the mid-longitudinal axes $L_1$ and $L_2$. The operation of the telescoping column 80, the motor and transmission portion 96, and the motor and transmission portion 102 can be controlled by the one or more controllers of the surgical platform system 10 and/or the robotic system R.

Figure 1C:
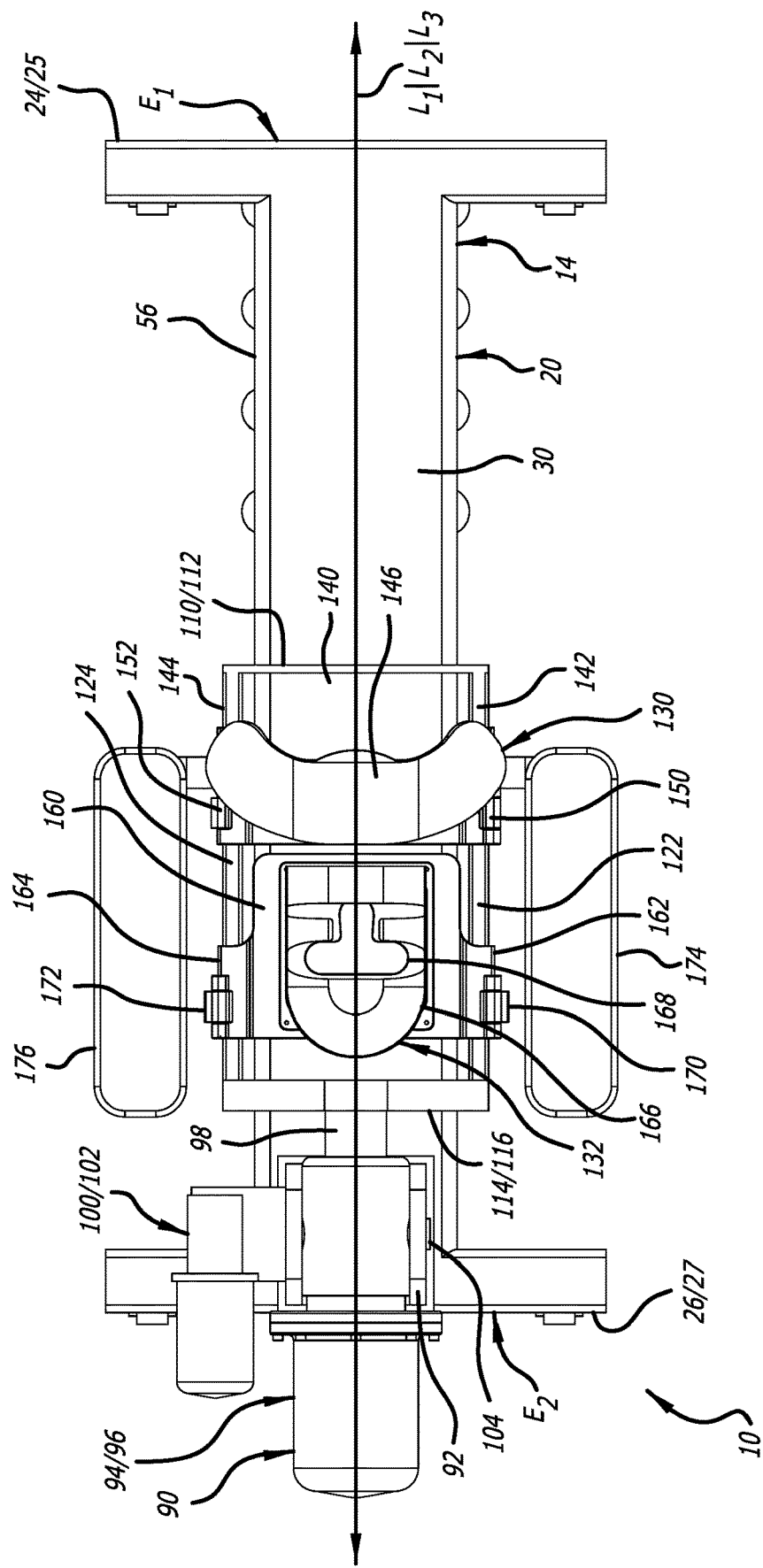
FIG. 1C is a top, plan view that illustrates the first portion of the surgical platform system of FIG. 1A.
Figure 2:
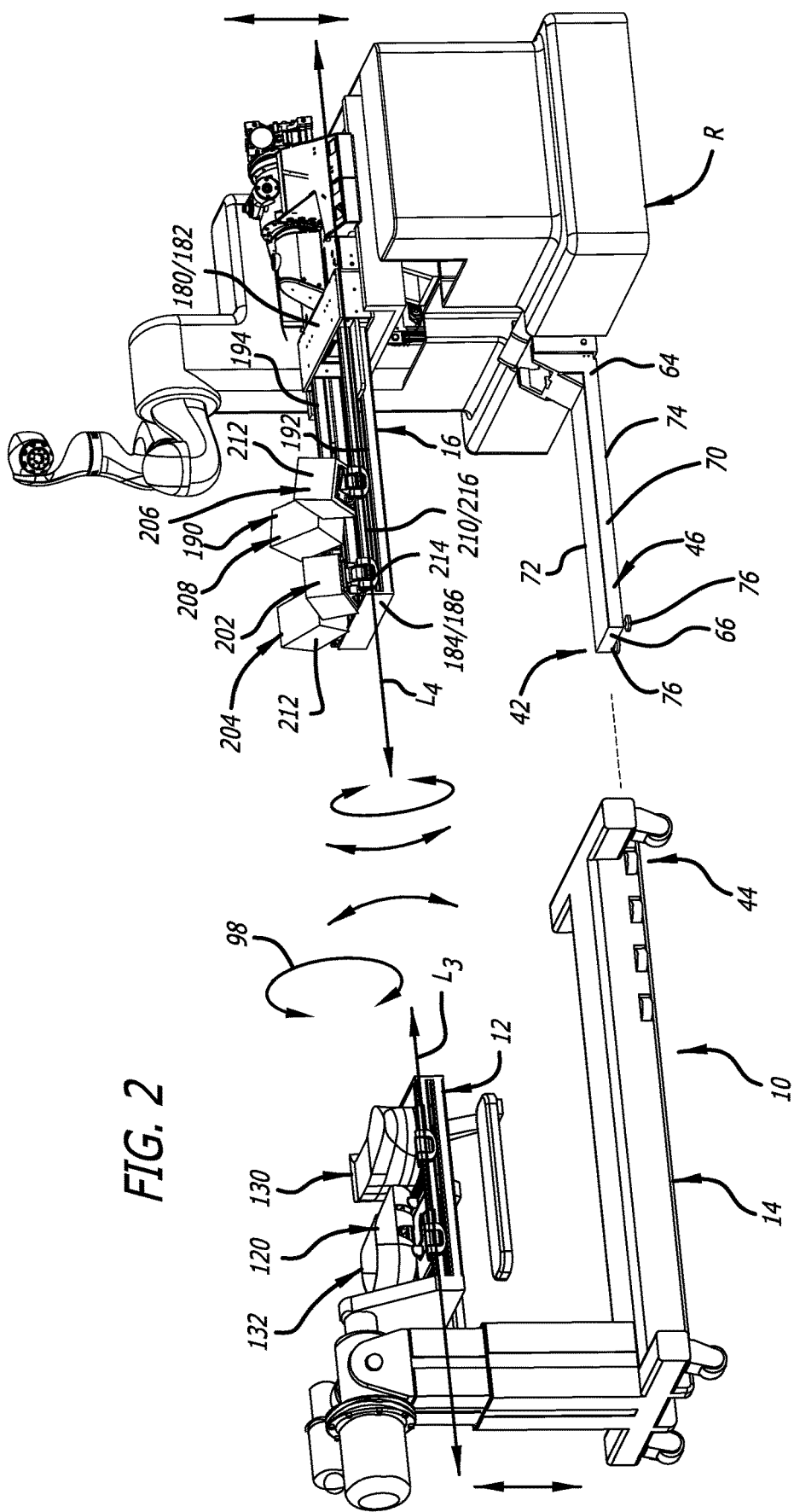
FIG. 2 is a side, perspective view that illustrates the first portion of the surgical platform system of FIG. 1A being positioned relative to a second portion of the surgical platform system and a surgical robotic system supporting the second portion of the surgical platform system.

As depicted in FIGS. 1B and 1C, the first platform portion 12 includes a first end portion 110 at and adjacent a first end 112 thereof, a second end portion 114 at and adjacent a second end 116 thereof, and various rails positioned therebetween that connect the first end portion 110 and the second end portion 114 to one another. The second end portion 114 has a height (FIG. 1B) sufficient enough to afford attachment relative to the axle 98, and such attachment affords rotation of the first platform portion 12 via operation of the motor and transmission portion 96. The first platform portion 12 includes a first patient support portion 120, and the various rails, as depicted in FIGS. 1B and 1C, can include a first outer rail 122 and a second outer rail 124 that extend between the first end portion 110 and the second end portion 114. First end portions of the first outer rail 122 and the second outer rail 124 can be attached to the first end portion 110, opposite second end portions of the first outer rail 122 and the second outer rail 124 can be attached to the second end portion 112, and/or the first and second end portions can be attached to intermediate portions (not shown) positioned between the various rails and the first end portion 110 and/or the second end portion 114. Furthermore, the first outer rail 122 and the second outer rail 124 can be aligned with a mid-longitudinal axis $L_3$ of the first platform portion 12 with the first outer rail 122 being positioned on one side of the mid-longitudinal axis $L_3$, and the second outer rail 124 being positioned on the other side of the mid-longitudinal axis $L_3$.

In addition to providing structural rigidity to the first platform portion 12, the first outer rail 122 and the second outer rail 124 can also be used to support the first patient support portion 120 of the first platform portion 12. The at least one patient support portion 120 can include a chest support portion 130 and a head support portion 132 that are integrated with or separate from one another. As depicted in FIGS. 1B and 1C, the chest support portion 130 and the head support portion 132 are separate from one another. Furthermore, the chest support portion 130 and/or the head support portion 132 can be moveably adjusted or fixed in position along portions of the first outer rail 122 and the second outer rail 124 to accommodate differently-sized patients. As depicted in FIGS. 1B and 1C, the chest support portion 130 and the head support portion 132 are moveably adjustable along the first outer rail 122 and the second outer rail 124. And, as depicted in FIGS. 1B and C, the patient P is supported in a prone position by the first patient support portion 120, with the upper torso of the patient P being contacted to and supported by the chest support portion 130, and the head of the patient P being contacted to and supported by the head support portion 132. As such, the first outer rail 122 and the second outer rail 124 serve as tracks affording movement of the chest support portion 130 and the head support portion 132.

The chest support portion 130, as depicted in FIG. 1C, includes a first platen portion 140, a first lateral side portion 142 attached relative to a first lateral side of the first platen portion 140, and a second lateral side portion 144 attached relative to a second lateral side of the first platen portion 140. The first platen portion 140 can extend between the first lateral side portion 142 and the second lateral side portion 144, and, using the first lateral side portion 142 and the second lateral side portion 144, the first platen portion 140 can be supported between the first outer rail 122 and the second outer rail 124. The first platen portion 140 can be used to support chest support padding 146 thereon.

As depicted in FIG. 1C, the first lateral side portion 142 can contact and be moveably supported by the first outer rail 122, and the second lateral side portion 144 can contact and be moveably supported by the second outer rail 124. The first lateral side portion 142 can include a first clamping portion 150 attached thereto, and the second lateral side portion 144 can include a second clamping portion 152 attached thereto that can, respectively, be engaged and disengaged relative to the first outer rail 122 and the second outer rail 124. Engagement of the first clamping portion 150 and the second clamping portion 152 maintains the first lateral side portion 142 and the second lateral side portion 144 (and the first platen portion 140) in position relative to the first outer rail 122 and the second outer rail 124, respectively, and disengagement of the first clamping portion 150 and the second clamping portion 152 allows movement of the first lateral side portion 142 and the second lateral side portion 144 (and the first platen portion 140) along the first outer rail 122 and the second outer rail 124, respectively. As such, the chest support padding 146 can be positioned and repositioned to accommodate patients of different sizes to find an acceptable position to support the patient's upper torso, and then the chest support padding 146 can be maintained in position using the first clamping portion 150 and the second clamping portion 152. The chest support padding 146 can deform to cushion portions of the patient's upper torso, and in doing so, also serve in maintaining the position of the patient's upper torso relative to the first platform portion 12.

In similar fashion to the chest support portion 130, the head support portion 132 can include a second platen portion 160, a first lateral side portion 162 attached relative to a first lateral side of the second platen portion 160, and a second lateral side portion 164 attached relative to a second lateral side of the second platen portion 160. The second platen portion 160 can extend between the first lateral side portion 162 and the second lateral side portion 164, and, using the first lateral side portion 162 and the second lateral side portion 164, the second platen portion 160 can be supported between the first outer inner rail 122 and the second outer rail 124. As depicted in FIG. 1C, the second platen portion 160 can be used to support head support 166, and can include an aperture 168 formed therein that can provide access to the airways of the patient P.

As depicted in FIG. 1C, the first lateral side portion 162 can contact and be moveably supported by the first outer rail 122, and the second lateral side portion 164 can contact and be moveably supported by the second outer rail 124. The first lateral side portion 162 can include a first clamping portion 170 attached thereto, and the second lateral side portion 164 can include a second clamping portion 172 attached thereto that can, respectively, be engaged and disengaged relative to the first outer rail 122 and the second outer rail 124. Engagement of the first clamping portion 170 and the second clamping portion 172 maintains the first lateral side portion 162 and the second lateral side portion 164 (and the second platen portion 160) in position relative to the first outer rail 122 and the second outer rail 124, respectively, and disengagement of the first clamping portion 170 and the second clamping portion 172 allows movement of the first lateral side portion 162 and the second lateral side portion 164 (and the second platen portion 160) along the first outer rail 122 and the second outer rail 124, respectively. As such, the head support 166 can be positioned and repositioned to accommodate patients of different sizes to find an acceptable position to support the patient's head, and then the head support 166 can be maintained in position using the first clamping portion 170 and the second clamping portion 172. The head support 166 can serve in maintaining the position of the patient's head relative to the first platform portion 12.

If the chest support portion 130 and the head support portion 132 are integrated with one another, the chest support portion 130 (and corresponding support padding) and the head support portion 132 (and corresponding support) can be included on a single platen (not shown) that can be moveably supported by the first outer rail 122 and the second outer rail 124, and also the chest support portion 130 and/or the head support portion 132 could be moveably supported relative to the single platen. The single platen, as well as the chest support portion and the head support portion when moveably supported by the single platen, can also include one or more clamping portions attached thereto for maintaining the single platen, the chest support portion, and/or the head support portion in position.

In addition to the chest support portion 130 and the head support portion 132, first and second arm supports 174 and 176 can be provided as part of the first platform portion 12 to support arms of the patient P relative to the remaining portions thereof. As depicted in FIGS. 1B, the first arm support 174 is attached relative to the first outer rail portion 122, and the second arm support 176 is attached relative to the second outer rail portion 124. As such, when the upper torso of the patient P is supported by the chest support portion 130 and the head of the patient P is supported by the head support portion 132, the left arm and the right arm of the patient P can be supported relative to the remainder of the first platform portion 12 by the first arm support 174 and the second arm support 176, respectively.

As depicted in FIGS. 2, the second platform portion 16 includes a first end portion 180 at and adjacent a first end 182 thereof, a second end portion 184 at and adjacent a second end 186 thereof, and various rails positioned therebetween that connect the first end portion 180 and the second end portion 184 to one another. The first end portion 184 can be attached to the robotic system R or a sub-system (not shown) positioned relative to the robotic system, and the robotic system R or the sub-system can be used to adjust upwardly and downwardly, rotate, and/or tilt the second platform portion 16 via operation thereof in similar directions as afforded by use of the telescoping column 80 and the rotational/tilt positioner 90. Rather being provided as part of the robotic system, a portion of the positioner 42 can alternatively be provided as part of the sub-system.

The second platform portion 16 includes a second patient support portion 190, and the various rails, as depicted in FIG. 2, can include a first outer rail 192 and a second outer rail 194 that extend between the first end portion 180 and the second end portion 184. First end portions of the first outer rail 192 and the second outer rail 194 can be attached to the first end portion 180, opposite second end portions of the first outer rail 192 and the second outer rail 194 can be attached to the second end portion 180, and/or the first and second end portions can be attached to intermediate portions (not shown) positioned between the various rails and the first end portion 180 and/or the second end portion 184. Furthermore, the first outer rail 192 and the second outer rail 194 can be aligned with a mid-longitudinal axis $L_4$ of the second platform portion 16 with the first outer rail 192 being positioned on one side of the mid-longitudinal axis $L_4$, and the second outer rail 194 being positioned on the other side of the mid-longitudinal axis $L_4$.

In addition to providing structural rigidity to the second platform portion 16, the first outer rail 192 and the second outer rail 194 can also be used to support the second patient support portion 190 that can include a first upper thigh support 202, a second upper thigh support 204, a first lower thigh support 206, and a second lower thigh support 208 used to contact and support the upper legs of the patient P. The first upper thigh support 202, the second upper thigh support 204, the first lower thigh support 206, and the second lower thigh support 208 can be moveably adjusted or fixed in position along portions of the first outer rail 192 and the second outer rail 194 to accommodate differently-sized patients. As depicted in FIG. 2, the first upper thigh support 202 and the first lower thigh support 206 are supported by the first outer rail 192, and the second upper thigh support 204 and the second lower thigh support 208 are supported by the second outer rail 194. As such, the first outer rail 192 and the second outer rail 194 serve as tracks affording movement of the first upper thigh support 202, the second upper thigh support 204, the first lower thigh support 206, and the second lower thigh support 208.

The first upper thigh support 202, the second upper thigh support 204, the first lower thigh support 206, and the second lower thigh support 208 can each include bracket portions 210, support padding 212, and clamping portions 214. The bracket portions 210 of the first upper thigh support 202, the second upper thigh support 204, the first lower thigh support 206, and the second lower thigh support 208 can be moveably supported relative to at least one of the first outer rail 192 and the second outer rail 194. The bracket portions 210 can each include plate portions 216 for supporting the support padding 212, and the plate portions 216 of the first upper thigh support 202, the second upper thigh support 204, the first lower thigh support 206, and/or the second lower thigh support 208 can have different angles with respect to the remainders of the bracket portions 210 to orient the support padding 212 differently. The clamping portions 214, like the clamping portions discussed above, can be engaged and disengaged to the first outer rail 192 and/or the second outer rail 194 to maintain the positions thereof or allow the positioning and repositioning therealong. As such, the first upper thigh support 202, the second upper thigh support 204, the first lower thigh support 206, and the second lower thigh support 208 can be adjusted into position to accommodate patients of different sizes, and then the first upper thigh support 202, the second upper thigh support 204, the first lower thigh support 206, and the second lower thigh support 208 can be maintained in position using the clamping portions 214. The support padding 212 can deform to cushion portions of the patient's thighs, and in doing so, also serve in maintaining the position of the patient's thighs relative to the first platform portion 12.

In addition to the first upper thigh support 202, the second upper thigh support 204, the first lower thigh support 206, and/or the second lower thigh support 208, a lower leg support (not shown) of the second patient support portion 190 can be provided. The lower leg support can be used to contact and support the lower legs of the patient P, and can include a plate portion (not shown) and support padding (not shown). The plate portion, for example, can be positioned between and supported by the first outer rail 192 and the second outer rail 194, and the support padding can be supported by the plate portion. The plate portion of the lower leg support can be fixed in position relative to the first outer rail 192 and the second outer rail 194. However, like the other various patient support portions, the plate portion can be moveably supported relative to the remainder of the second platform portion 16 to afford positioning and repositioning thereof. Furthermore, the lower leg support could also include one or more clamping portions that can be engaged and disengaged. As such, the lower leg support can be adjusted into position to accommodate patients of different sizes, and then the lower leg support can be maintained in position using the one or more clamping portions.

With the surgical platform system 10 positioned relative to the robotic system R and/or the sub-system such that the receiver portion 44 and the tongue portion 46 of the positioner 42 are engaged with one another, the patient P, as depicted in FIGS. 4-10, can be received on the first platform portion 12 and the second platform portion 16. To accommodate differently-sized patients components of the first patient support portion 120 (including the chest support portion 130 and the head support portion 132), and/or the second patient support portion 190 (including the first upper thigh support 202, the second upper thigh support 204, the first lower thigh support 206, the second lower thigh support 208, and/or the lower leg support) can be positioned and repositioned along the first platform portion 12 and the second platform portion 16. As depicted in FIGS. 4-10, the head and torso of the patient P are supported by the first platform portion 12, and the upper and lower legs of the patient P are supported by the second platform portion 16, and components of the first patient support portion 120 and the second patient support portion 190 are positioned to contact and support the corresponding portions of the patient P relative to the first platform portion 12 and the second platform portion 16.

While the head and upper torso of the patient P are supported by the first patient support portion 120 on the first platform portion 12, and the upper and lower legs of the patient P are supported by the second patient support portion 190 on the second platform portion 16 in FIGS. 4-10, the position of the patient P could be reversed with the first patient support portion 120 supporting the head and upper torso of the patient P on the second platform portion 16, and the second patient support portion 190 supporting the upper and lower legs of the patient P on the first platform portion 12. Furthermore, while the patient is supported in the prone position in FIGS. 4-10, the patient P could be supported in the supine position on the first platform portion 12 and the second platform portion 16.

With a first portion of the patient P supported by the first platform portion 12 and a second portion of the patient P supported by the second platform portion 16, the first platform portion 12 and the second platform portion 16 can be be independently adjusted relative to another to position/orient and reposition/reorient these portions of the patient P supported thereby before, during, and after surgery. The independent adjustment of the relative positions of the first platform portion 12 and the second platform portion 16 is afforded by the separation therebetween defined by the gap G.

To illustrate, the first platform portion 12 can be raised and lowered via operation of the telescoping column 80, can be rotated by actuation of the rotational portion 94 via rotation of the corresponding axle 98 via operation of the corresponding motor and transmission portion 96, and can be titled by actuation of the tilt portion 100 via rotation of the corresponding axle 104 via operation of the corresponding motor and transmission portion 102. The upward and downward movement afforded by the telescoping column 80, the rotational movement afforded by the rotational portion 94, and the tilting movement of the first platform portion 12 afforded by the tilt portion 100 serve to position and reposition first platform portion 12 to position/orient and reposition/reorient the first portion of the patient P supported thereby relative to the second platform portion 16 (and the second portion of the patient P supported by the second platform portion 16). And the second platform portion 16 likewise can be moved upwardly and downwardly, rotated, and tilted by the robotic system R or the sub-system in similar fashion to the first platform portion 12 to position and reposition the second platform portion 16 to position/orient and reposition/reorient the second portion of the patient P supported thereby relative to the first platform portion 12 (and the first portion of the patient P supported by the first platform portion 12).

Figure 7:
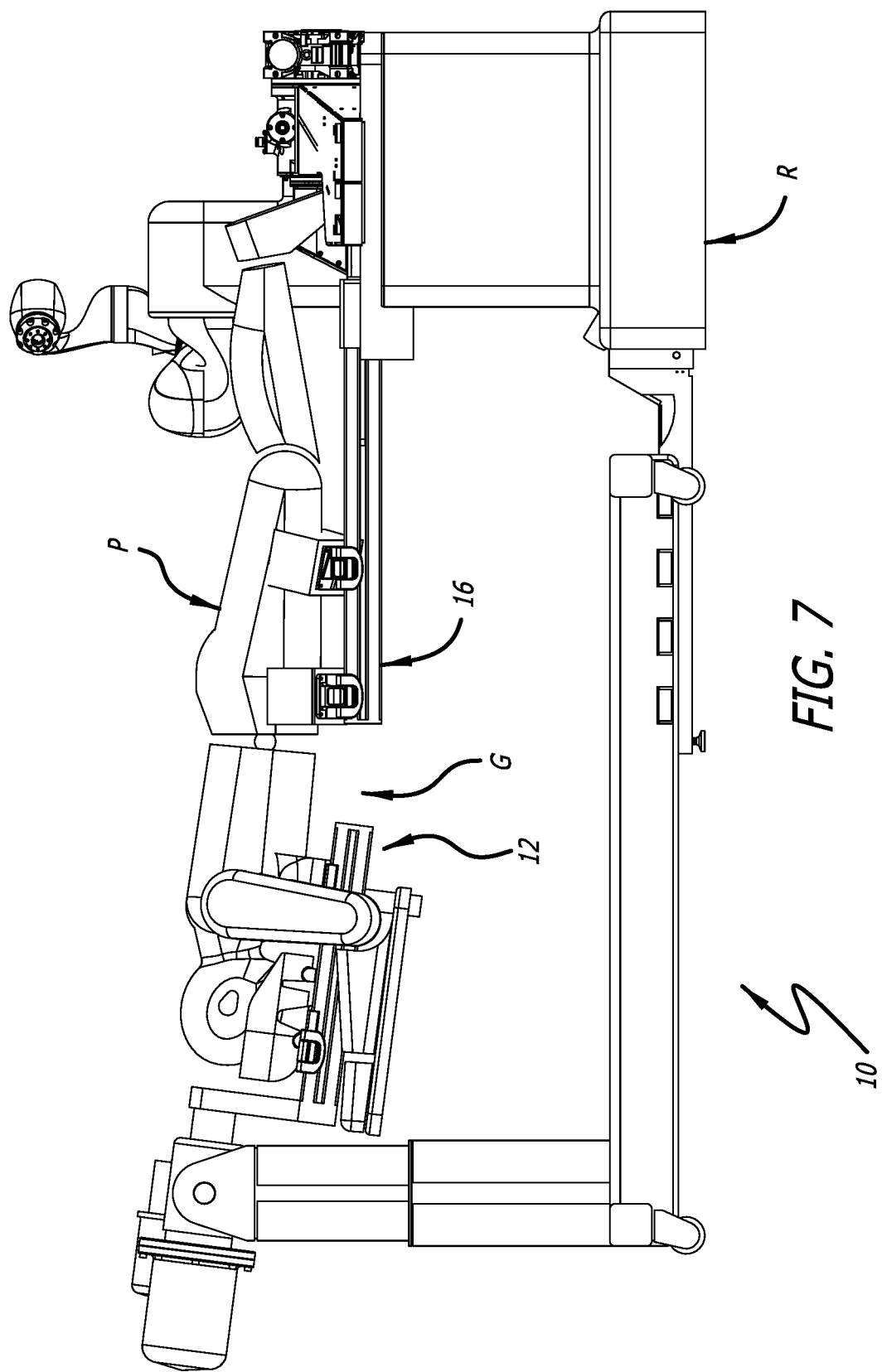
FIG. 7 is a side, elevational view that illustrates the first portion of the surgical platform system of FIG. 1A and a first portion of the patient supported thereon raised and tilted downwardly relative to the second portion of the surgical platform system of FIG. 3 and a second portion of the patient positioned thereon.
Figure 8:
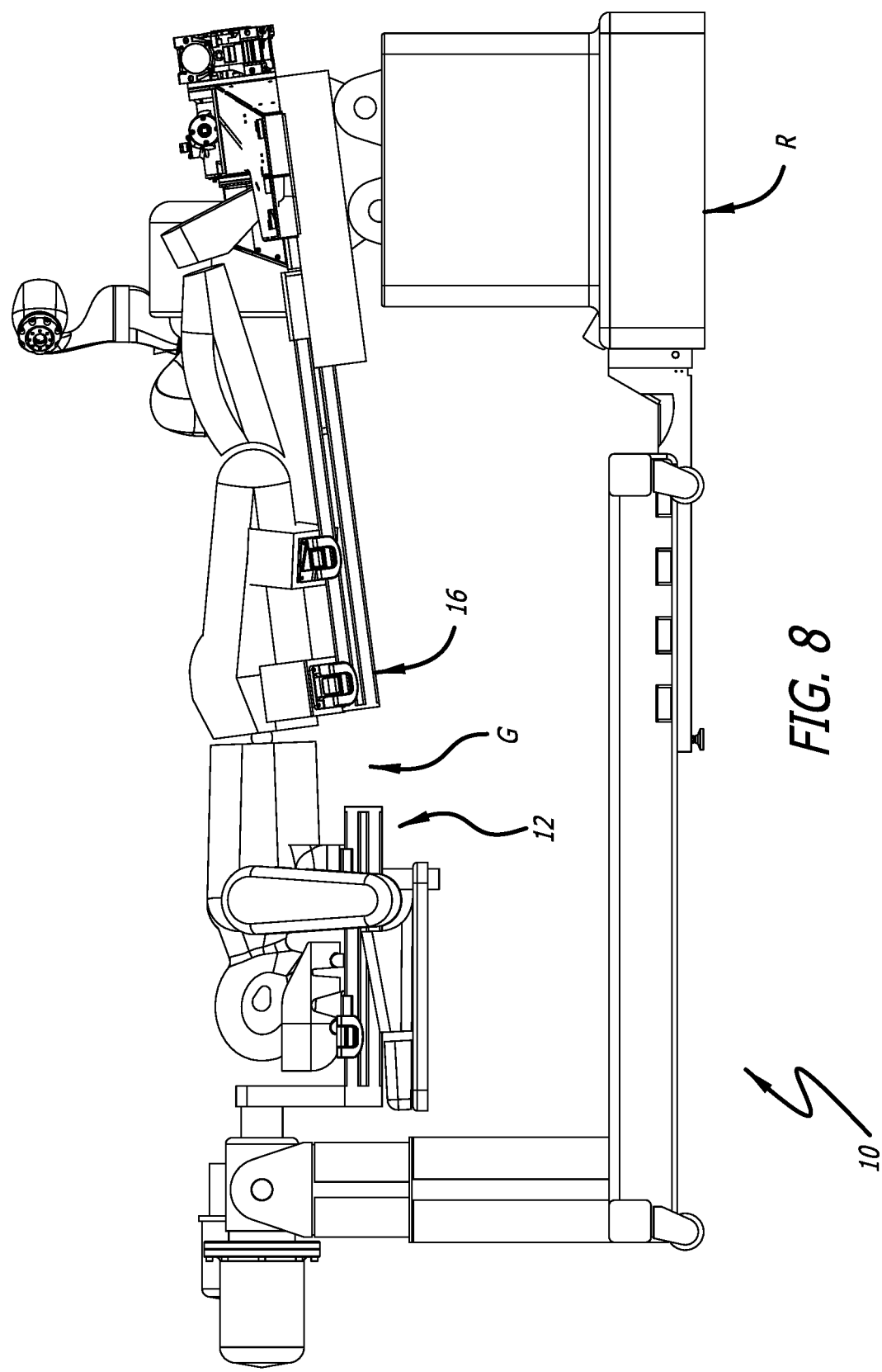
FIG. 8 is a side, elevational view that illustrates the second portion of the surgical platform system of FIG. 3 and the second portion of the patient supported thereon raised and tilted downwardly relative to the first position of the surgical platform system of FIG. 1A and the first position of the patient positioned thereon.
Figure 9:
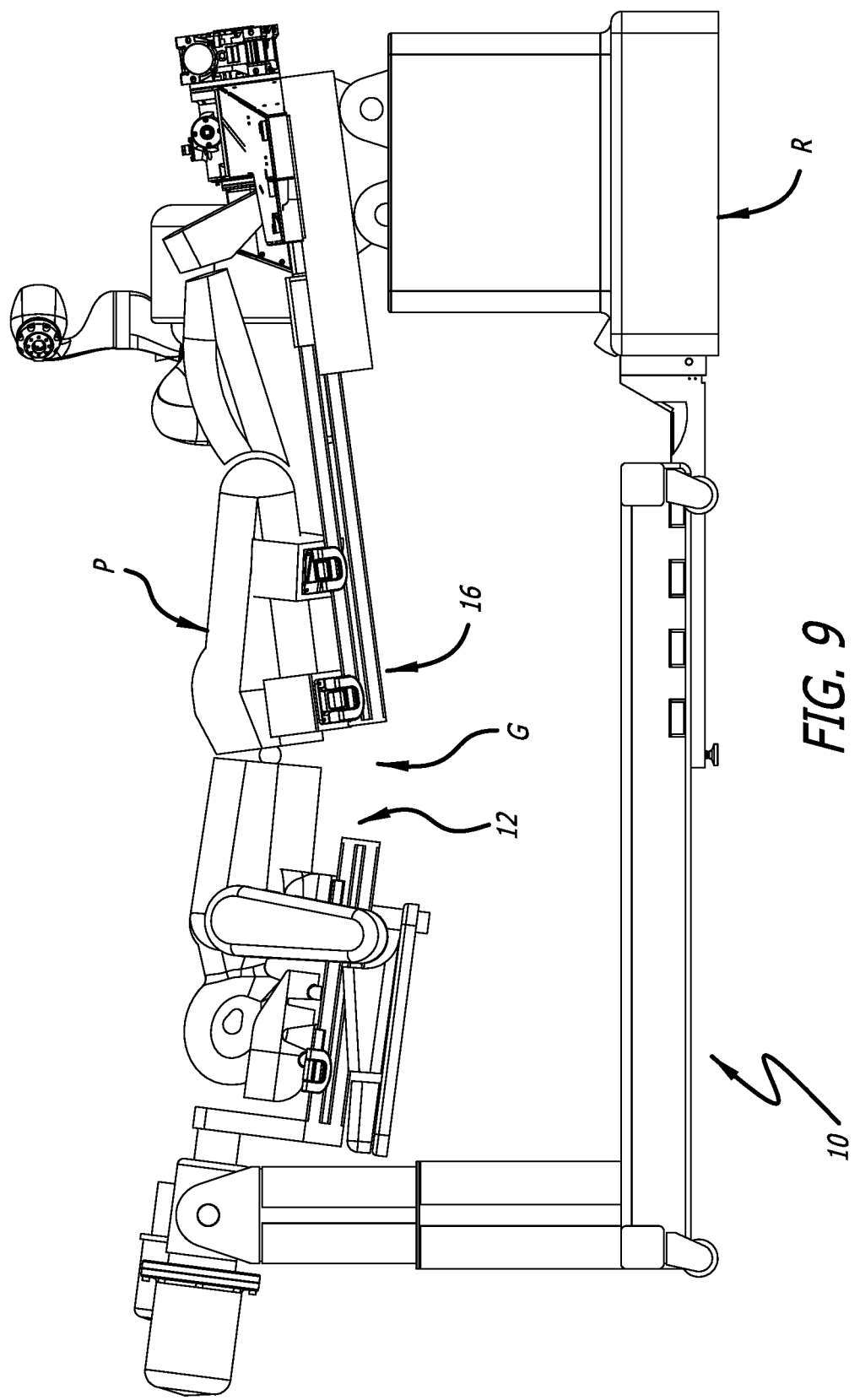
FIG. 9 is a side, elevational view that illustrates the first and second portions of the surgical platform system of FIG.

The independent and relative movement of the first platform portion 12 and the second platform portion 16 can be used to adjust the position/orientation of the portions of patient P supported thereby before, during, and after surgery, and the robotic system R can be used for performing surgery or facilitating performance of surgery on the patient P. For example, as depicted in FIG. 7, the telescoping column 80 could be actuated to raise the position of the first platform portion 12 and the tilt portion 100 could be actuated to tilt the position of the first platform portion 12, and in doing so, bend the patient's body to tilt the head and upper torso upwardly relative to the legs. Similarly, as depicted in FIG. 8, the robotic system R or sub-system could be actuated to raise and tilt the position of the second platform portion 16, and in doing so, bend the patient's body to tilt the legs upwardly relative to the head and upper torso. And, as depicted in FIG. 9, the positions/orientations of the first support platform 12 and the second support platform 16 via actuation of the telescoping column, the tilt portion 100, and the robotic system R can be adjusted to bend the patient's body to both move the head and upper torso upwardly and/or move the legs upwardly. The articulation of the patient's body in FIGS. 7-9 introduces degrees of extension to the patient's spine.

Additionally, the positions/orientations of the first support platform 12 and the second support platform 16 via actuation of the telescoping column 80, the tilt portion 100, and the robotic system R or sub-system alternatively can be adjusted to bend the patient's body to move the head and upper torso downwardly and/or move the legs downwardly to introduce degrees of flexion to the patient's spine. And, the first portion of the patient's body supported by the first platform portion 12 and the second portion of the patient's body support by the second platform portion 16 can be twisted relative to one another to introduce torsion therebetween via actuation of the rotational portion 94 and/or the robotic system R or sub-system. Furthermore, the telescoping column 80 or the robotic system R or sub-system can also be actuated (without tilting or twisting) to raise the first portion of patient's body supported by the first platform portion 12 relative to the second portion of the patient's body supported by the second platform portion 16 (FIG. 11), or vice versa. And, the patient's body can be stretched (FIG. 12) or contracted by adjusting the position of the support portion 14 varying the amount of insertion of the tongue portion 46 into the receiving area $A_1$.

Accordingly, the actuation of the telescoping column 80, the rotational portion 94, tilt portion 100, and the robotic system R or sub-system can be used to adjust the relative positions and orientations of the first platform portion 12 and the second platform portion 16 to correspondingly adjust the position/orientation of the patient's body before, during, and after surgery. Furthermore, the surgical platform system 10, the robotic system R, and/or the sub-system can include the one or more controllers for controlling actuatable portions thereof in the surgical platform system 10, the robotic system R, and/or the sub-system to facilitate the operation thereof to coordinate movement therebetween. And such coordinated movement via the one or more controllers, for example, can be used to manipulate and prevent over-extension or over-flexion of the spine of the patient before, during, and after surgery. Thereafter, when the surgery is complete, the patient P can be removed from the first platform portion 12 and the second platform portion 16, and the first surgical platform 12 can be disconnected relative to the robotic system R or the sub-system.

As depicted in FIGS. 13 and 16-21, the modified surgical platform system 10' is provided that affords additional movement and manipulation of the patient P in comparison to the surgical platform system 10. The modified surgical platform system 10' is similar to and includes many features of the surgical platform 10, and like numbering is used to describe the similar features. To illustrate, the modified surgical platform system 10' includes the first platform portion 12 and the second platform portion 16. However, the modified surgical platform system 10' affords additional side-to-side and rotational movement of the first platform portion 12 relative to the second platform portion 16.

The modified surgical platform system 10', as depicted in FIG. 13, includes a support portion 230 that includes a horizontally-oriented portion 232 that supports the vertically-oriented portion 22. Like the horizontally-oriented portion 20, the horizontally-oriented portion 232 includes the first end member 24 at the first end 25 thereof, the cross member 30 extending from first end member 24 toward the second end 27, the mid-longitudinal axis $L_2$ extending through the first end 25 and the second end 27, and a portion of the positioner 42 (i.e., the receiver portion 44. Instead of the second end member 26, the horizontally-oriented portion 232 includes an end portion 234 at the second end 27 thereof.

As depicted in FIG. 14, the end portion 234 supports the vertically-oriented portion 22, and includes a slider portion 240 and a rotator portion 242. As discussed below, the slider portion 240 is configured to move the vertically-oriented portion 22 in directions transverse to the mid-longitudinal axis $L_2$, and the rotator portion 242 is configured to rotate the vertically-oriented portion 22. The end portion 234, as depicted in FIG. 15, includes a bottom portion 250, an endwall portion 252, a first sidewall portion 254, and a second sidewall portion 256. The end portion 234 includes an open end 258 adjacent the second end 27, and together, the bottom portion 250, the endwall portion 252, the first sidewall portion 254, and the second sidewall portion 256 define an area in which the slider portion 240 and the rotator portion 242 are provided.

The first sidewall portion 254 and the second sidewall portion 256, as depicted in FIGS. 14 and 15, can include indentations 260 and 262 that include undersurfaces 264 and 266, respectively. Casters 268 can be attached to each of the undersurfaces 264 and 266, and together with the casters 40, the casters 268 can be used to space the end portion 234 from the ground and to facilitate movement of the support portion 230 thereon.

The slider portion 240, as depicted in FIG. 15, can include a first track portion 270, a second track portion 272, one or more first trucks 274 moveable along the first track portion 270, one or more second trucks 276 moveable along the second track portion 272, and a platform portion 278 supported by the first trucks 274 and the second trucks 276. Using movement of the first trucks 274 and the second trucks 276 on the first track portion 270 and the second track portion 272, respectively, the platform portion 278 is moveable relative to the bottom portion 250 in a side-to-side direction transverse to the mid-longitudinal axis $L_2$ between a first position and a second position. In the first position, a majority of the platform portion 278 can be located on one side of the mid-longitudinal axis $L_2$, and, in the second position, a majority of the platform portion 278 can be located on the other side of the mid-longitudinal axis $L_2$.

Linear movement of the platform portion 278 can be controlled via operation of a linear actuator 280 that includes a motor and transmission portion 282 that is actuatable to move a telescoping arm portion 284 inwardly and outwardly. The telescoping arm portion 284 is attached to an extension portion 286 that extends outwardly from the platform portion 278. As such, the inward movement and the outward movement of the telescoping arm portion 284 serves to move the platform portion 278 between the first position and the second position thereof. Accordingly, the first platform portion 12 can be moved in side-to-side directions relative to the mid-longitudinal axis $L_2$ via actuation of the actuator 280 of the slider portion 240. In some embodiments, for example, one or more controllers of the surgical platform system 10' and/or the robotic system R can be used in actuating the actuator 280 to control movement of the first platform portion 12.

The platform portion 278, as depicted in FIG. 15, can support the rotator portion 242 thereon, and the rotator portion 242 can support the vertically-oriented portion 22 thereon. The rotator portion 242 can include a base portion 290, a rotatable portion 292, and an actuator 294. Rotation of the rotatable portion 292 can be controlled via operation of the actuator 294 that includes a motor and transmission portion that is actuatable to rotate the rotatable portion 292 and the vertically-oriented portion 22 supported by the rotatable portion 292 about a vertically-oriented axis. Accordingly, the first platform portion 12 can be rotated via actuation of the actuator 294 of the rotator portion 242. In some embodiments, for example, the one or more controllers of the surgical platform system 10' and/or the robotic system R can be used in actuating the actuator 294 to control movement of the first platform portion 12.

As depicted in FIGS. 16 and 17, with a first portion (including the first platform portion 12) of the surgical platform system 10' positioned relative to a second portion (including the second platform portion 16) of the surgical platform system 10' attached relative to the robotic system R and/or the sub-system, such that the receiver portion 44 and the tongue portion 46 of the positioner 42 are engaged with one another, the patient P can be received on and supported by the first platform portion 12 and the second platform portion 16. In doing so, the first patient support portion 120 (including the chest support portion 130 and the head support portion 132), and the second patient support portion 190 (including the first upper thigh support 202, the second upper thigh support 204, the first lower thigh support 206, the second lower thigh support 208, and/or the lower leg support) can be positioned to accommodate the size of the patient P. Thereafter, the first platform portion 12 and the second platform portion 16 can be independently adjusted relative to another to position/orient and reposition/reorient portions of the patient supported thereby. And use of the slider portion 240 and the rotator portion 242 affords additional degrees of adjustment of the first platform portion 12 relative to the second platform portion 16 of the surgical platform system 10' in comparison to the surgical platform system 10.

To adjust the position of the first platform portion 12 relative to the surgical platform system 10', the telescoping column 80 can be actuated for expansion and contraction via telescoping movement of the upper portion 84 relative to the lower portion 82 between a lower position and an upper position, and such movement correspondingly moves the first platform portion 12 upwardly and downwardly. In addition, the rotational portion 94 can be actuated via operation of the motor and transmission 96 to rotate the first platform portion 12 of the surgical platform system 10', and the tilt portion 100 can be actuated via operation of the motor and transmission 102 to tilt the first platform portion 12 of the surgical platform system 10'. Additionally, the slider portion 240 can be actuated via operation of the motor and transmission 282 to move the first platform portion 12 of the surgical platform system 10' in a direction transverse to the mid-longitudinal axis $L_2$, and the rotator portion 242 can be actuated via operation of the motor and transmission 294 to rotate the first platform portion 12 about a vertically-oriented axis. The one or more controllers of the surgical platform system 10' and/or the robotic system R can be used in controlling such actuation.

The upward and downward movement afforded by the telescoping column 80, the rotational movement afforded the rotational portion 94, the tilting movement afforded by the tilt portion 100, the side-to-side movement afforded by the slider portion 240, and the rotational movement afforded by the rotator portion 242 serves to position/orient and reposition/reorient first platform portion 12 of the surgical platform system 10' to correspondingly position/orient and reposition/reorient the portions of the patient supported thereby relative to the second platform portion 16. And the second platform portion 16 likewise can be moved upwardly and downwardly, rotated, and tilted via actuation of the robotic system R or the sub-system (in similar fashion to the first platform portion 12) to correspondingly position/orient and reposition/reorient the portions of the patient supported thereby relative to the first platform portion 12. The one or more controllers of the surgical platform system 10' and/or the robotic system R can be used in controlling such actuation.

While the head and upper torso of the patient P are supported by the first patient support portion 120 on the first platform portion 12, and the upper and lower legs of the patient P are supported by the second patient support portion 190 on the second platform portion 16 in FIGS. 16-21, the position of the patient P could be reversed with the first patient support portion 120 supporting the head and upper torso of the patient P on the second platform portion 16, and the second patient support portion 190 supporting the upper and lower legs of the patient P on the first platform portion 12. Furthermore, while the patient is supported in the prone position in FIGS. 16-21, the patient P could be supported in the supine position on the first platform portion 12 and the second platform portion 16.

With a first portion of the patient P supported by the first platform portion 12 and a second portion of the patient P supported by the second platform portion 16, the first platform portion 12 and the second platform portion 16 can be independently adjusted relative to another to position/orient and reposition/reorient the portions of the patient P supported thereby before, during, and after surgery. The independent adjustment of the relative positions of the first platform portion 12 and the second platform portion 16 is afforded by the separation therebetween defined by the gap G.

For example, the telescoping column 80 could be actuated to raise the position of the first platform portion 12 and the tilt portion 100 could be actuated to tilt the position of the first platform portion 12, and in doing so, bend the patient's body to tilt the head and upper torso upwardly relative to the legs (in similar fashion to that depicted in FIG. 7). Similarly, the robotic system R or sub-system could be actuated to raise and tilt the position of the second platform portion 16, and in doing so, bend the patient's body to tilt the legs upwardly relative to the head and upper torso (in similar fashion to that depicted in FIG. 8). Furthermore, the first support platform 12 and the second support platform 16 could be positioned/oriented to both tilt the head and upper torso of the patient P upwardly and tilt the legs of the patient P upwardly (in similar fashion to that depicted in FIG. 9). Accordingly, the positions/orientations of the first support platform 12 and the second support platform 16 via actuation of the telescoping column 80, the tilt portion 100, and the robotic system R can be adjusted to bend the patient's body to move the head and upper torso upwardly and/or move the legs upwardly to introduce degrees of extension to the patient's spine.

Furthermore, the positions/orientations of the first support platform 12 and the second support platform 16 via actuation of the telescoping column 80, the tilt portion 100, and the robotic system R or sub-system alternatively can be adjusted to bend the patient's body to move the head and upper torso downwardly and/or move the legs downwardly to introduce degrees of flexion to the patient's spine (in similar fashion to that depicted in FIG. 10). And, the first portion of the patient's body supported by the first platform portion 12 and the second portion of the patient's body supported by the second platform portion 16 can be twisted relative to one another to introduce torsion therebetween via actuation of the rotational portion 94 and/or the robotic system R or sub-system. Furthermore, the telescoping column 80 or the robotic system R or sub-system can also be actuated (without tilting or twisting) to raise the first portion of patient's body supported by the first platform portion 12 relative to the second portion of the patient's body supported by the second platform portion 16 (in similar fashion to that depicted in FIG. 11), or vice versa. And, the patient's body can be stretched (in similar fashion to that depicted in FIG. 12) or contracted by adjusting the position of the support portion 14 by varying the amount of insertion of the tongue portion 46 into the receiving area $A_1$.

The modified surgical platform system 10' provides additional degrees of adjustment in comparison to the first surgical platform 10. As discussed above, the slider portion 240 can be actuated via operation of the motor and transmission 282 to move the first platform portion 12 of the surgical platform system 10' in a direction transverse to the mid-longitudinal axis $L_2$, and the rotator portion 242 can be actuated via operation of the motor and transmission 294 to rotate the first platform portion 12 about a vertically-oriented axis. As such, the sagittal position/orientation of the patient P can be adjusted, as depicted in FIGS. 19 and 20, via relative adjustment of the first platform portion 12 with respect to the second platform portion 16 using the slider portion 240 and the rotator portion 242. Additionally, the first platform portion 12 can be rotated via actuation of the rotational portion 94, and the torsional position/orientation of the patient P can be adjusted, as depicted in FIG. 21, via relative adjustment of the first platform portion 12 with respect to the second platform portion 16 using the rotational portion 94.

Accordingly, the actuation of the telescoping column 80, the rotational portion 94, tilt portion 100, the slider portion 240, the rotational portion 242, and/or the robotic system R or sub-system can be used to adjust the relative positions and orientations of the first platform portion 12 and the second platform portion 16. And the relative movement of the first platform portion 12 and the second platform portion 16 can be used to adjust the position/orientation of the patient's body P before, during, and after surgery, and the robotic system R can be used for performing surgery or facilitating performance of surgery on the patient. As discussed above, the surgical platform system 10', the robotic system R, and/or the sub-system can include a controller or controllers for controlling actuatable portions thereof in the surgical platform system 10', the robotic system R, and/or the sub-system to facilitate the operation thereof to coordinate movement therebetween. And such coordinated movement via the controller or controllers, for example, can be used to manipulate and prevent over-extension or over-flexion of the spine of the patient before, during, and after surgery. Thereafter, when the surgery is complete, the patient can be removed from the first platform portion 12 and the second platform portion 16, and the surgical platform 12 can be disconnected relative to the robotic system R or the sub-system.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

We claim:

1. A surgical platform system comprising:
    a first platform portion and a support portion supporting the first platform portion,
        the support portion including a first support structure, a second support structure, and an adjustment portion, the first support structure having a first end, an opposite second end, a mid-longitudinal axis extending through the first end and the second end of the first support structure, a first end portion at the first end of the first support structure, a second end portion at the second end of the first support structure, and at least one cross member extending between the first end portion and the second end portion of the first support structure, the second end portion including a slider portion and a rotator portion supported by the slider portion, the second support structure extending upwardly from the rotator portion of the first support structure, the second support structure vertically spacing the adjustment portion apart from the first support structure, and the adjustment portion rotatably and tiltably supporting the first platform portion relative to the first support structure and the second support structure; and the first platform portion including a first end, an opposite second end, a first end portion at the first end of the first platform portion, a second end portion at the second end of the first platform portion, at least a first rail and a second rail extending between the first end portion and the second end portion of the first platform portion, a head support, and a chest support supported by the at least the first rail and the second rail of the first platform portion; and
    a second platform portion including a first end, an opposite second end, a first end portion at the first end of the second platform portion, a second end portion at the second end of the second platform portion, at least a first rail and a second rail extending between the first end portion and the second end portion of the second platform portion, and at least a first thigh support and a second thigh support supported by the at least the first rail and the second rail of the second platform portion;
    wherein the support portion is positionable relative to a robotic system, and the first end portion of the second platform portion is supported relative to the robotic system;
    wherein, when the support portion is positioned relative to the robotic system, the first platform portion and the second platform portion are positioned adjacent to one another and separated by a gap between the first end of the first platform portion and the second end of the second platform portion; and
    wherein the first platform portion is moveable side-to-side across the mid-longitudinal axis via operation of the slider portion, the first platform portion is rotatable about an axis transverse to the mid-longitudinal axis via operation of the rotator portion, and the first platform portion is at least one of tiltable upwardly/downwardly and rotatable about an axis aligned with the mid-longitudinal axis via operation of the adjustment portion in order to position/orient and reposition/orient a first portion of a patient supported by the first platform portion relative to a second portion of the patient supported by the second platform portion.

2. The surgical platform of claim 1, wherein the second support structure is expandable and contractible between a first height and a second height to correspondingly move the first platform portion upwardly and downwardly relative to the first support structure.

3. The surgical platform of claim 1, further comprising at least one platen supporting the head support and the chest support, the at least one platen being supported between the at least the first rail and the second rail of the first platform portion.

4. The surgical platform of claim 1, wherein at least one of the head support, the chest support, the first thigh support, and the second thigh support are each adjustable relative to the at least the first rails and the second rails of a respective one of the first platform portion and the second platform portion to accommodate patients of different sizes.

5. The surgical platform of claim 1, wherein the adjustment portion is configured to tilt the first end of the first platform portion upwardly and downwardly relative to the first support structure, and configured to rotate the first platform portion side-to-side relative to the first support structure.

6. The surgical platform of claim 1, further comprising a first positioner portion attached to the first support structure and a second positioner portion attached relative to the robotic system, and engagement of the first positioner portion and the second positioner portion initially positions the support portion relative to the robotic system.

7. The surgical platform of claim 6, wherein positioning of the first support structure relative to robotic system via positioning of the first positioner portion relative to the second positioner portion correspondingly adjusts a length of the first platform portion and the second platform portion to accommodate patients of different sizes.

8. The surgical platform of claim 1, wherein the second platform portion is at least one of moveable upwardly/downwardly, rotatable, and tiltable by the robotic system relative to the first platform portion.

9. A surgical platform system comprising:
a first platform portion and a support portion,
the support portion supporting the first platform portion above and vertically spacing the first platform portion apart from the ground, the support portion including an end portion including a slider portion and a rotator portion supported by the slider portion, a vertical portion extending upwardly from the rotator portion, and an adjustment portion supported by the vertical portion, the first platform portion being rotatably and tiltably connected to the adjustment portion; and
the first platform portion including a first end, an opposite second end, a first end portion at the first end of the first platform portion, a second end portion at the second end of the first platform portion, at least a first rail and a second rail extending between the first end portion and the second end portion of the first platform portion, a head support, and a chest support supported by the at least the first rail and the second rail of the first platform portion; and
a second platform portion including a first end, an opposite second end, a first end portion at the first end of the second platform portion, a second end portion at the second end of the second platform portion, at least a first rail and a second rail extending between the first end portion and the second end portion of the second platform portion, and at least a first thigh support and a second thigh support supported by the at least the first rail and the second rail of the second platform portion;
wherein the support portion is positionable relative to a robotic system, and the first end portion of the second platform portion is supported relative to the robotic system;
wherein, when the support portion is positioned relative to the robotic system, the first platform portion and the second platform portion are positioned adjacent to one another and separated by a gap between the first end of the first platform portion and the second end of the second platform portion; and
wherein the first platform portion is moveable side-to-side via operation of the slider portion, the first platform portion is rotatable about an axis transverse to the mid-longitudinal axis via operation of the rotator portion, and the first platform portion is at least one of tiltable upwardly/downwardly and rotatable via operation of the adjustment portion in order to position/orient and reposition/reorient a first portion of a patient supported by the first platform portion relative to a second portion of the patient supported by the second platform portion.

10. The surgical platform of claim 9, wherein a portion of the support portion is expandable and contractible between a first height and a second height to correspondingly move the first platform portion upwardly and downwardly relative to portions of the support portion.

11. The surgical platform of claim 9, further comprising at least one platen supporting the head support and the chest support, the at least one platen being supported between the at least the first rail and the second rail of the first platform portion.

12. The surgical platform of claim 9, wherein the adjustment portion is configured to tilt the first end of the first platform portion upwardly and downwardly relative to the ground, and configured to rotate the first platform portion side-to-side relative to the ground.

13. The surgical platform of claim 9, further comprising a first positioner portion attached to the support portion and a second positioner portion attached relative to the robotic system, and engagement of the first positioner portion and the second positioner portion initially positions the support portion relative to the robotic system.

14. The surgical platform of claim 9, wherein the second platform portion is at least one of moveable upwardly/downwardly, rotatable, and tiltable by the robotic system relative to the first platform portion.

15. A surgical platform system comprising:
a first platform portion and a support portion supporting the first platform portion,
the support portion including a first support structure, a second support structure, and an adjustment portion, the first support structure having a first end, an opposite second end, a mid-longitudinal axis extending through the first end and the second end of the first support structure, a first end portion at the first end of the first support structure, a second end portion at the second end of the first support structure, and at least one cross member extending between the first end portion and the second end portion of the first support structure, the second end portion including a slider portion and a rotator portion supported by the slider portion, the second support structure extending upwardly from the rotator portion of the first support structure, the second support structure vertically spacing the adjustment portion apart from the first support structure, and the adjustment portion rotatably and tiltably supporting the first platform portion relative to the first support structure and the second support structure; and
the first platform portion including a first end, an opposite second end, and a length between the first end and the second end of the first platform portion, the first platform portion being configured to support a first portion of a patient thereon; and
a second platform portion including a first end, an opposite second end, and a length between the first end and the second end of the second platform portion, the second platform portion being configured to support a second portion of the patient thereon;
wherein, when the support portion is positioned relative to the robotic system, the first platform portion and the second platform portion are positioned adjacent to one another and separated by a gap between the first end of the first platform portion and the second end of the second platform portion; and
wherein the first platform portion is moveable side-to-side across the mid-longitudinal axis via operation of the slider portion, the first platform portion is rotatable about an axis transverse to the mid-longitudinal axis via operation of the rotator portion, and the first platform portion is at least one of tiltable upwardly/downwardly and rotatable about an axis aligned with the mid-longitudinal axis via operation of the adjustment portion in order to position/orient and reposition/reorient the first and second portions of the patient supported by the first platform portion and the second platform portion relative to one another.

16. The surgical platform of claim 15, wherein the second support structure is expandable and contractible between a first height and a second height to correspondingly move the first platform portion upwardly and downwardly relative to the first support structure.

17. The surgical platform of claim 15, wherein the adjustment portion is configured to tilt the first end of the first platform portion upwardly and downwardly relative to the first support structure, and configured to rotate the first platform portion side-to-side relative to the first support structure.

18. The surgical platform of claim 15, further comprising a first positioner portion attached to the first support structure and a second positioner portion attached relative to the robotic system, and engagement of the first positioner portion and the second positioner portion initially positions the support portion relative to the robotic system.

19. The surgical platform of claim 18, wherein the first positioner portion includes a first plate portion and a second plate portion spaced apart from one another, and defines with an undersurface of the first support structure a cavity, and the second positioner portion includes a tongue portion extending outwardly relative to the robotic system, the tongue portion being receivable within the cavity to position the support portion relative to the robotic system.

20. The surgical platform of claim 18, wherein positioning of the first support structure relative to robotic system via positioning of the first positioner portion relative to the second positioner portion correspondingly adjusts a length of the first platform portion and the second platform portion to accommodate patients of different sizes.

* * * * *